United States Patent [19]

Szántay et al.

[11] Patent Number: 4,843,080

[45] Date of Patent: Jun. 27, 1989

[54] 1,12B-DISUBSTITUTED OCTAHYDROINDOLO[2,3-A]QUINOLIZINE DERIVATIVES, PHARMACEUTICAL COMPOSITIONS

[75] Inventors: Csaba Szántay; Ferenc Sóti; Maria Incze; Zsuzsanna Balogh née Kardos; Zsolt Szombathelyi; Egon Kárpáti, all of Budapest; Béla Kiss, Vecsés; Katalin Csomor, Budapest; István Laszlovszky, Budapest; Erzsébet Lapis, Budapest; Lilla Forgács, Budapest; Csaba Kuthi, Budapest; László Szporny, Budapest, all of Hungary

[73] Assignee: Richter Gedeon Vegyeszeti Gyar Rt., Budapest, Hungary

[21] Appl. No.: 853,353

[22] Filed: Apr. 17, 1986

[30] Foreign Application Priority Data

Apr. 19, 1985 [HU] Hungary .................. 1517/85

[51] Int. Cl.⁴ .................. C07D 471/08; A61K 31/40
[52] U.S. Cl. .................. 514/285; 546/70
[58] Field of Search .................. 546/70; 514/285

[56] References Cited

U.S. PATENT DOCUMENTS

| | | | |
|---|---|---|---|
| 3,478,051 | 0/0000 | Houlihan et al. | |
| 4,173,642 | 11/1979 | Szantay et al. | 546/70 |
| 4,353,911 | 10/1982 | Buzas | 546/70 X |
| 4,358,452 | 11/1982 | Opalko | 546/70 |
| 4,429,129 | 1/1984 | Szantay et al. | 546/70 |
| 4,464,534 | 8/1984 | Szantay et al. | 546/70 |

OTHER PUBLICATIONS

Chem. Abstracts, vol. 69, 10387V (1968) which is an Abstract of Shiroyan et al., Arm. Khim. Zh. vol. 20, pp. 649–658, (1967).
Shiroyan et al., Arm. Khim. Zh. vol. 26, pp. 147–152, (1973).
Shiroyan et al., Arm. Khim. Zh. vol. 25, pp. 61–65, (1972).
Chem. Abstracts vol. 97, 72271q (1982), which is an Abstract of Avetyan et al., Khim-Pharm. Zh. vol. 16, pp. 556–560, (1982).
Taniguchi et al., Chem. Pharm. Bull., vol. 31, pp. 1856–1865, (1983).
Taniguchi et al., Chem. Pharm. Bull., vol. 32, pp. 2544–2554, (1984).
Szantay et al., Synthesis, pp. 354–356 (1974).
Abramovitch, et al., J. Chem. Soc., pp. 4593–4592 (1956).
Abramovitch, J. Chem. Soc., pp. 4593–4602 (1956).
Spaeth et al., B 63, 2102–2111 (1930).
Potts et al., J. Chem. Soc., pp. 2641–2643 (1954).
Clark et al., J. C. S., Perkin I. pp. 1743–1745, (1977).
Durst et al., J. Org. Chem., vol. 39, pp. 3271–3273, (1974).
Ando et al., Chem. Letters, vol. 45, pp. 45–46, (1979).
Taylor et al., J. Am. Chem. Soc., vol. 90, pp. 2421–2422, (1968).
Oikawa et al., J. Org. Chem., vol. 43, pp. 2087–2088, (1978).
Walborsky, J. Am. Chem. Soc., vol. 71, p. 2941, (1949).
Krieger, J. Am. Chem. Soc., vol. 71, pp. 3156–3171, (1949).
Adkins et al., J. Am. Chem., Soc., vol. 52, pp. 3212–3221, (1930).
Sprague et al., J. Am. Chem. Soc., vol. 56, pp. 2665–2668, (1934).

*Primary Examiner*—Anton H. Sutto
*Assistant Examiner*—Andrew G. Rozycki
*Attorney, Agent, or Firm*—Herbert Dubno; Jonathan Myers

[57] ABSTRACT

The invention relates to new racemic and optically active 1,12b-disubstituted octahydroindolo[2,3-a]quinolizine derivatives of the formula (I)

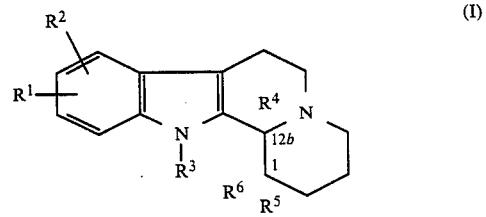

wherein
$R^1$ and $R^2$ are the same or different and represent hydrogen, halogen, nitro, alkyl having from 1 to 6 carbon atoms, alkoxy having from 1 to 6 carbon atoms or hydroxyl,
$R^3$ and $R^5$ are the same or different and represent hydrogen, alkyl having from 1 to 6 carbon atoms or aralkyl having from 1 to 6 carbon atoms in the alkyl moiety,
$R^4$ is alkyl having from 1 to 6 carbon atoms, aryl or aralkyl having from 1 to 6 carbon atoms in the alkyl moiety, and
$R^6$ is an electron attracting substituent, and cis and trans isomers and acid addition salts thereof.

The compounds are pharmaceutically active, in particular show an outstanding cardiovascular, e.g. selective peripheral vasodilating activity. Some of these compounds are valuable intermediates in the preparation of other, pharmaceutically active compounds.

4 Claims, No Drawings

1,12-DISUBSTITUTED OCTAHYDROINDOLO[2,3-]QUINOLIZINE DERIVATIVES, PHARMACEUTICAL COMPOSITIONS

The invention relates to new racemic and optically active 1,12b-disubstituted octahydroindolo[2,3-a]quinolizine derivatives of the formula (I)

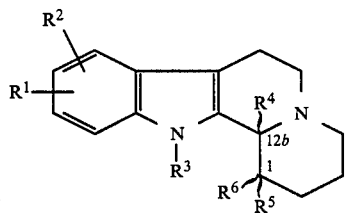

wherein
$R^1$ and $R^2$ are the same or different and represent hydrogen, halogen, nitro, alkyl having from 1 to 6 carbon atoms, alkoxy having from 1 to 6 carbon atoms or hydroxyl, $R^3$ and $R^5$ are the same or different and represent hydrogen, alkyl having from 1 to 6 carbon atoms or aralkyl having from 1 to 6 carbon atoms in the alkyl moiety, $R^4$ is alkyl having from 1 to 6 carbon atoms, aryl or aralkyl having from 1 to 6 carbon atoms in the alkyl moiety, and $R^6$ is an electron attracting substituent, and cis and trans isomers and acid addition salts thereof.

The compounds of the formula (I) are valuable intermediates in the preparation of other, pharmaceutically active compounds, and are pharmaceutically active themselves, in particular show cardiovascular, especially peripheral vasodilating activity. According to another aspect of the invention there are provided pharmaceutical compositions containing, as active ingredient, at least one compound of the formula (I) as hereinbefore defined, or a physiologically compatible acid addition salt thereof, in association with conventional pharmaceutical carriers and/or excipients.

According to a still further aspect of the invention there is provided a process for the preparation of the racemic and optically active compounds of the formula (I), wherein $R^1$, $R^2$, $R^3$, $R^4$, $R^5$ and $R^6$ are as defined above, cis and trans isomers and acid addition salts thereof, by
condensing a ketone derivative of the formula (III)

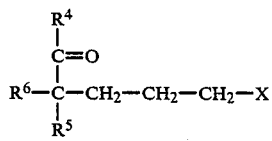

wherein $R^4$, $R^5$ and $R^6$ are as defined above and X is a leaving group, with a tryptamine derivative of the formula (II)

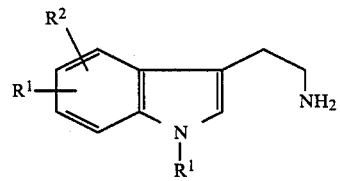

wherein $R^1$, $R^2$ and $R^3$ are as defined above, and
if $R^5$ is other than hydrogen, subjecting the tryptamine derivative of the formula (V)

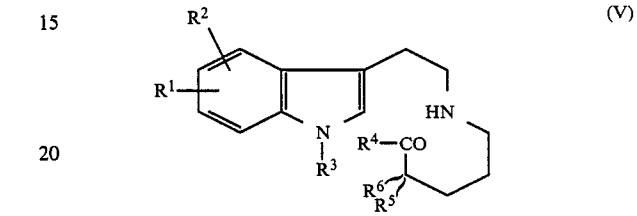

obtained, in which $R^1$, $R^2$, $R^3$, $R^4$, $R^5$ and $R^6$ are as defined above, to cyclization, optionally after isolation, or
if $R^5$ is hydrogen, subjecting the N-indolylethyltetrahydropyridine derivative of the formula (VI)

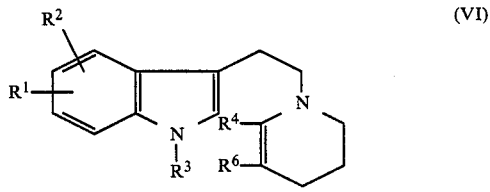

obtained, in which $R^1$, $R^2$, $R^3$, $R^4$ and $R^6$ are as defined above, to cyclization, and if desired,
subjecting a 1,12b-disubstituted octahydroindolo[2,3-a]quinolizine derivative of the formula (I) obtained, in which $R^1$ and/or $R^2$ are hydrogen and $R^3$, $R^4$, $R^5$ and $R^6$ have the same meanings as defined above, to halogenation and/or nitration, and/or if desired,
alkylating a 1,12b-disubstituted octahydroindolo[2,3-a]quinolizine derivative of the formula (I) obtained, in which $R^3$ and/or $R^5$ are hydrogen and $R^1$, $R^2$, $R^4$ and $R^6$ have the same meanings as defined above, and/or if desired,
treating a compound of the formula (I), in which $R^1$, $R^2$, $R^3$, $R^4$, $R^5$ and $R^6$ are as defined above, with an acid or
treating an acid addition salt of a compound of the formula (I), in which $R^1$, $R^2$, $R^3$, $R^4$, $R^5$ and $R^6$ are as defined above, with a base, and/or if desired,
separating a cis/trans isomeric mixture obtained into the respective isomers and/or if desired,
subjecting a racemic 1,12b-disubstituted octahydroindolo[2,3-a]quinolizine derivative of the formula (I) to resolution.

In the above formulae $R^1$ and $R^2$ as halogen represent any halogen atom, such as fluorine, chlorine, bromine or iodine;

$R^1$, $R^2$, $R^3$, $R^4$ and $R^5$ as an "alkyl having from 1 to 6 carbon atoms" stand for any straight-chained or branched alkyl group having from 1 to 6 carbon atoms, e.g. methyl, ethyl, n-propyl, isopropyl, n-butyl, sec.- butyl, isobutyl, tert.-butyl, n-pentyl, isopentyl, n-hexyl, isohexyl, etc.;

$R^1$ and $R^2$ as an "alkoxy having from 1 to 6 carbon atoms" are the oxy-derivatives of any of the above-identified alkyl groups;

in the definition of $R^3$, $R^4$ and $R^5$ the term "aralkyl having from 1 to 6 carbon atoms in the alkyl moiety" is used to define a combination of any of the above alkyl groups with a mono- or multicyclic, isolated or condensed aromatic group, e.g. phenyl, diphenyl, naphthyl, etc.;

$R^4$ as an "aryl" group stands for any of the aryl groups defined in connection with the aralkyl groups; and in the definition of $R^6$ the electron attracting group preferably is an alkoxycarbonyl, alkylcarbonyl, aralkylcarbonyl or arylcarbonyl group, each containing from 1 to 6 carbon atoms in the alkyl and alkoxy moieties, in which the alkoxy, alkyl, aralkyl and aryl moieties are as defined above.

X as a leaving group represents any group, which is split off during the reaction with the compound of the formula (II). Thus X may stand for halogen as defined in connection with $R^1$ and $R^2$, alkylsulfonyl, e.g. methanesulfonyl; or arylsulfonyl optionally substituted with alkyl, e.g. p-toluene-sulfonyl or benzenesulfonyl.

Compounds of the formula (I) as well as their preparation are new. In the literature there are disclosed merely 12b-substituted 1,2,3,4,5,7,12,12b-octahydroindolo[2,3-a]quinolizine derivatives, which do not contain an electron attracting substituent on the carbon atom at the 1-position, and they are prepared from other starting materials in a different route. For example, Shiroyan et al. [Arm. Khim. Zh. 20, 649 (1967)] reacted 2-oxo-6-methyl-2,3-dihydropyrane with tryptamine to yield γ-acetyl-N-indolylethyl-butyric acid amide, which was converted into 12b-methyl-4-oxo-1,2,3,4,6,7,12,12b-octahydroindolo[2,3-a]quinolizine by cyclization in an acidic medium, and finally its carbonyl group was reduced to methylene with lithium-aluminium hydride. A similar process was described by Houlihaneat et al. [United States Patent Specification No. 3,478,051], in which 4-benzoyl-butyric acid was acylated with tryptamine, and the compound obtained was cyclized in an acidic medium and subsequently reduced with lithium-aluminium hydride on its acid amide function, to yield 12b-phenyl-1,2,3,4,6,7,12,12b-octahydroindolo[2,3-a]quinolizine. These methods are, however, not suitable for the preparation of the compounds according to the invention. On the other hand, there are numerous indolo[2,3-a]quinolizine compounds substituted on the 12b-carbon atom by an alkyl or aryl substituent, which contain for example a methoxy substituent in the ring A [F. R. Shiroyan et al.: Arm. Khim. Zh. 26, 147 (1973); 27, 61 (1974)], an alkyl group attached to the 1-carbon atom [F. R. Shiroyan et al.: Arm. Khim. Zh., 25, 61 (1972)], and an alkyl or aralkyl group on the indole nitrogen [V. T. Anetyan et al: Khim. Farm. 16, 556 (1982)], none of them contains, however, an electron attracting substituent on the 1-carbon atom. These known compounds were also prepared by one of the above-described known processes.

By the process according to the invention the new compounds of the formula (I) can be prepared from commercially available starting materials or from compounds which are easy to prepare, in a simple route. The process according to the invention is substantially different from the methods known in the art for the preparation of structurally related compounds. By the instant process some of the substituents may be incorporated into the desired compounds subsequent to the ring closure as well.

In the compounds of the formula (III) the presence of $R^6$, i.e. of the electron attracting substituent to be attached to the 1-carbon atom of the indolo[2,3-a]quinolizine skeleton in the compounds of the formula (I) is significant in many respects. On the one hand, it is due to this group that the substituted ketones of the formula (III) are easy to prepare. These compounds of the formula (III) preferably are β-ketoesters or β-diketones, and therefore their propyl side-chain containing a leaving group in the γ-position, necessary for the formation of the ring D can be easily prepared by the well known, widely employed acetacetic ester or by an analogous synthesis, and the incorporation of a possible $R^5$ substituent is also very simple. On the other hand, the electron attracting substituent makes the formation of 12b-substituted indolo[2,3-a]quinolizine skeleton substantially easier. Finally, the subsequent substitution of the 1-carbon atom and the subsequent conversions of the compounds of the formula (I) into other pharmaceutically active compounds are rendered possible by this substituent.

Most of the tryptamine derivatives of the formula (II) used as starting material in the process according to the invention are commercially available and can be prepared by methods known in the art. A good summary of these methods is to be found in Beilsteins Handbuch der organischen Chemie, 22, Supplements 1, 2 and 3–4, Syst. Nr. 3395 and for example in the following publications selected at random. Preparation of tryptamine derivatives substituted in the phenyl ring: M. Taniguchi et al., Chem. Pharm. Bull., 31, 1856 (1983); 32, 2544 (1984); Cs. Szántay et al., Synthesis 354 (1974); R. A. Abramovitch, D. Shapiro, J. Chem. Soc., 4589 (1956); R. A. Abramovitch, J. Chem. Soc., 4595 (1956); E. Spät, E. Lederer, B 63, 2102 (1930); preparation of tryptamine derivatives substituted on the indole nitrogen: E. Spät, E. Lederer, B 63, 2102 (1930); K. T. Potts, J. E. Saxton, J. Chem. Soc. 2641 (1954).

The substituted ketones of the formula (III) used as a reaction component in the process according to the invention are partly known, partly new, which can be prepared from the β-ketoesters of the formula (IV)

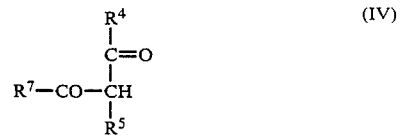

wherein $R^4$ and $R^5$ are as defined in connection with formula (I), $R^7$ is an alkoxy group having from 1 to 6 carbon atoms, or from the respective β-diketones, in which $R^4$ and $R^5$ are as defined in connection with formula (I), and $R^7$ is alkyl having from 1 to 6 carbon atoms, aryl or aralkyl having from 1 to 6 carbon atoms in the alkyl moiety, by the well known and widely used acetacetic ester synthesis or in an analogous manner, using 1,3-dihalopropane, e.g. 1,3-chlorobromopropane. If in the compounds of the formula (IV) $R^5$ is hydrogen, the alkyl or aralkyl group can be incorporated into the molecule again with the acetacetic ester synthesis or by a similar reaction. These reactions are particularly easy to carry out by recently developed modern techniques

[e.g. J. H. Clark, J. M. Miller: J. C. S. Perkin I, 1743 (1977); H. D. Durst, L. Liebeskind: J. Org. Chem., 39, 3271 (1974); T. Ando, J. Yamawaki: Chem. Letters, 45 (1979); E. C. Tailor et al.: J. Am. Chem. Soc. 90, 2421 (1968)].

The 3-bromopropyl side-chain in the compounds of the formula (III) can be built up also by forming first an allyl group by acetacetic ester synthesis or in an analogous way in the compound of the formula (IV) and then additioning hydrogen bromide on the olefin bond, in the presence of benzoyl peroxide, according to the anti-Markownikow rule [as an analogous example for alkyl-malonic acid ester see: M. S. Schechter et al.: J. Am. Chem. Soc. 71, 3156 (1949); H. M. Walborsky: J. Am. Chem. Soc., 71, 2971 (1949)].

The 4-substituted acetacetic ester derivatives of the formula (IV) generally are commercially available but can easily be prepared also by the aid of the Meldrum acid (2,2-dimethyl-1,3-dioxane-2,6-dione) [as to this reaction see: Y. Oikawa et al.: J. Org. Chem., 43, 2087 (1978)]. The reaction can be carried out with an excellent yield.

The $\beta$-diketones of the formula (IV) either unsubstituted on the $\alpha$-carbon atom, either carrying an $R^5$ substituent are commercial products and can easily be prepared by methods known in the art [see e.g.: H. Adkins et al.: J. Am. Chem. Soc., 52, 3212 (1930); J. M. Sprague et al.: J. Am. Chem. Soc., 56, 2665 (1934)].

The compounds of the formula (III), in which X as a leaving group stands for an alkyl- or arylsulfonyl group can easily be prepared from the corresponding alcohols, i.e. compounds of the formula (III), in which X is hydroxyl by reaction with an alkylsulfonic acid chloride, e.g. methanesulfonic acid chloride; or arylsulfonic acid chloride, e.g. p-toluene-sulfonic acid chloride, in an inert organic solvent, e.g. chloroform, in the presence of an acid binding agent, such as triethyl amine.

An alternative method for the preparation of the $\beta$-diketones of the formula (III), in which $R^5$ is hydrogen consists in preparing a 6-$R^4$-5-($R^7$-carbonyl)-3,4-dihydro-2H-pyrane from a $\beta$-diketone of the formula (IV), in which $R^4$ and $R^7$ are as hereinabove defined and $R^5$ is hydrogen, by a 1,3-dihalopropane and treating the compound obtained with an acetic acid solution of hydrogen bromide to yield compounds of the formula (III), in which $R^4$ and $R^7$ are as defined above, $R^5$ is hydrogen and X is bromine. The 3,4-dihydro-2H-pyrane derivatives can for example be prepared by boiling a diketone of the formula (III) and 1,3-bromo-chloropropane in acetone, in the presence of potassium carbonate, and their purification can easily be achieved by distillation. In the acetic acid solution, under the effect of hydrogen bromide and boiling the dihydropyrane ring will be opened up in several hours, and the product obtained can be separated by distillation, following the elimination of acid traces.

According to the invention the indolo[2,3-a]quinolizine derivatives of the formula (I), in which $R^1$, $R^2$, $R^3$, $R^4$, $R^5$ and $R^6$ are as defined above, are prepared by condensing and cyclising a tryptamine derivative of the formula (II), in which $R^1$, $R^2$ and $R^3$ are as defined above, with a substituted ketone of the formula (III), in which $R^4$, $R^5$, $R^6$ and X are as defined above, in an inert organic solvent. Alternatively, the intermediate obtained by the condensation step can be separated, and the ring closure can be carried out as a separate reaction step. If $R^5$ has the same meanings as defined in connection with formula (I), except hydrogen, as a result of the above condensation a tryptamine derivative of the formula (V) can be isolated as an intermediate product, if, however, $R^5$ is hydrogen, this intermediate is immediately converted into the corresponding N-(indolylethyl)-1,4,5,6-tetrahydropyridine derivative of the formula (VI), which can be isolated, if desired. During the condensation as an inert organic solvent aromatic hydrocarbons, such as benzene, toluene, xylene, tetraline, biphenyl; halogenated hydrocarbons, such as carbon tetrachloride, chlorobenzene, bromobenzene; ethers having a high boiling point, e.g. diethyleneglycol dimethyl ether, di-n-butylether, diphenylether; preferably chlorobenzene can be employed. The acid binding agents used in the condensation step include tertiary bases, such as triethyl amine, N-ethyl-diisopropyl amine, N-methyl-morpholine, tributyl amine, etc. but an excess amount of the tryptamine derivative of the formula (II) can also be used for this purpose.

The advantage of the latter solution is that no new component is added to the reaction mixture, and from the salt obtained the tryptamine base of the formula (II) can be easily regenerated and recycled into the reaction. The condensation is carried out by heating at 50° to 180° C., preferably 100° to 140° C., preferably by boiling in the given solvent. The reaction time, depending on the reaction temperature, varies between 5 minutes and 48 hours. If $R^5$ is hydrogen, water is formed during the condensation, which is generally eliminated from the reaction mixture. This can be achieved by allowing the solvent employed to distill off slowly from the mixture which involves the elimination of the water, too, but a water separator may also be employed.

If $R^5$ is other than hydrogen, the cyclisation resulting the indolo[2,3-a]quinolizine skeleton starts already during the condensation and terminates during the subsequent heating, for example in chlorobenzene for 10 to 15 hours. Alternatively, the product of the formula (V) obtained as a result of condensation may be separated in an appropriate manner, e.g. by chromatography, and the ring closure may be accomplished in a separate reaction step, preferably by boiling in chlorobenzene. The compound of the formula (I) obtained can be isolated from the reaction mixture either as a base or as an acid addition salt by crystallization, or —preferably—by chromatography. Chromatography is preferably carried out on silica gel, with toluene containing 5 to 15% of diethyl amine. The end product of the formula (I), if desired, can be further purified by crystallization from hydrocarbons, preferably cyclohexane.

If $R^5$ is hydrogen, the ring closure yielding the indolo[2,3-a]quinolizine skeleton is preferably carried out by filtering off the insoluble acid addition salt of the compound of formula (II) formed in the condensation step, evaporating the mother liquor, dissolving the residue, containing the intermediate of the formula (VI), in a lower alcohol, preferably having from 1 to 6 carbon atoms, such as methanol, ethanol, propanol, isopropanol or butanol; cyclic ether, such as tetrahydrofurane, dioxane; an ether having a higher boiling point, e.g. diisopropyl ether, di-n-butyl ether, ethyleneglycol dimethyl ether or in another inert solvent or water or a mixture thereof, preferably in a mixture of dioxane and ethanol and acidifying the solution with a strong organic or inorganic acid. The cyclisation is performed at 0° C. to 100° C., preferably 20° C. to 80° C., and the reaction time is between 2 minutes and 48 hours, depending on the temperature and the reaction medium. As an organic acid for instance sulfonic acids, e.g. methanesulfonic acid, ethanesulfonic acid, p-toluene-sulfonic acid; optionally halogenated aliphatic carboxylic acids, such as halogenated acetic acid derivatives, e.g. trifluoroacetic acid can be employed, while the inorganic acids include hydrochloric acid, hydrobromic acid, phosphoric acid, sulfuric acid, perchloric acid, preferably hydrochloric acid.

In the ring closure step the acid is employed in an excess amount, preferably in a 5 to 25-fold excess related to the molar amount of the basic components present. The ring closure takes place between 2 minutes and 48 hours, depending on the acid employed and the reaction conditions. The product of the formula (I) is isolated as a base or as an acid addition salt by crystallization, or as a base by chromatography. If the product is isolated in the form of an acid addition salt, crystallization is preferably carried out from the solvent used in the ring closure step. If the product is isolated as a base, the reaction mixture of the ring closure is evaporated, the residue is admixed with water and a water-immiscible organic solvent, such as dichloromethane, chloroform, ethyl acetate, ether, toluene, preferably dichloromethane, whereupon it is rendered alkaline, preferably with sodium carbonate and the base is extracted from the mixture with the water-immiscible solvent employed. The base can be isolated from the solution in an appropriate manner, for example by evaporation, and if desired, can be further purified by crystallization.

If the product formed as a result of ring closure is isolated from the reaction mixture as an acid addition salt, the indolo[2,3-a]quinolizine derivative of the formula (I) can be set free from that salt in a known manner.

The cyclization yields the indolo[2,3-a]quinolizine derivatives of the formula (I) in the form of a cis-trans epimeric mixture, which can be separated by crystallization or chromatography, either as a base or in the form of a corresponding salt. The epimer formed in a larger amount is preferably isolated from the reaction mixture by crystallization, and the other epimer, formed in a lower amount, is then isolated from the base mixture isolated from the mother liquor, by chromatography. The optional step of isomer separation may be carried out after the cyclization or, alternatively, following the subsequent substitution.

If desired, the compounds of the formula (I), which do not carry the substituents $R^1$, $R^2$, $R^3$ and $R^5$ or are only partially substituted may be substituted by the substituents $R^1$ and/or $R^2$ or $R^3$ and/or $R^5$ also subsequent to the ring closure. In this case the base of the formula (I), in which $R^1$ and/or $R^2$ or $R^3$ and/or $R^5$ is hydrogen, or an acid addition salt thereof with an acid indifferent with respect to the desired substitution reaction, preferably the free base is dissolved in a solvent, in which the desired substitution reaction is to be carried out, the substitution is performed and the product obtained is isolated in an appropriate manner. If desired, the substitution reaction may be repeated with another substituent.

For example the ring A of the 1,2,3,4,6,7,12,12b-octahydroindolo[2,3-a]quinolizine skeleton of the compounds having the formula (I), in which $R^1$ and/or $R^2$ is hydrogen, may be subjected to subsequent halogenation and/or nitration. Or, for example, in the compounds of the formula (I), in which $R^5$ is hydrogen, the 1-carbon atom having an α-position related to the electron attracting substituent $R^6$ and/or in the compounds of the formula (I), in which $R^3$ is hydrogen the indole nitrogen atom may be alkylated in an additional reaction step. This subsequent substitution step may be repeated with another substituent, if desired.

The subsequent bromination of the ring A in the 1,12b-disubstituted octahydroindolo[2,3a]quinolizine compounds of the formula (I) may for example be carried out with N-bromo-succinimide, in a trifluoroacetic acid medium. The reaction is completed in several hours. The product is preferably isolated by converting the trifluoroacetic acid used as a solvent into a salt in an aqueous solution. This treatment is preferably carried out by rendering the reaction mixture alkaline with a 20% aqueous sodium carbonate solution, and separating the compound of the formula (I), which is present in a base form, from the trifluoroacetic acid sodium salt by extraction with a water-immiscible organic solvent, e.g. dichloromethane, chloroform, ether, toluene, preferably chloroform. The product may then be isolated from the organic solution in an appropriate manner, for example by evaporation and crystallization, or by chromatography. As a solvent for the purification by crystallization aliphatic, cyclic or aromatic hydrocarbons or mixtures thereof, preferably petroleum ether may be employed, while chromatography is preferably performed on silica gel, with petroleum ether containing 5 to 20% of diethyl amine.

The chlorination of the aromatic ring A is accomplished similarly to the bromination, if N-chlorosuccinimide is used as a chlorinating agent. But the ring A may be chlorinated also with sulfuryl chloride, or titanium (IV) chloride and an organic peracid, preferably m-chloro-perbenzoic acid, in an inert organic solvent, preferably dichloromethane, at room temperature. The product can be isolated by the decomposition of the reaction mixture with water, extraction of the chlorinated product and purification by chromatography.

The subsequent nitration of the ring A in the 1,12b-disubstituted-octahydroindo[2,3-a]quinolizine derivatives of the formula (I) can for example be carried out with fuming nitric acid, in an acetic acid solution. Preferably, an acetic acid solution of an indolo[2,3-a]quinolizine derivative of the formula (I) is added to the acetic acid solution of fuming nitric acid, at a temperature between $+10°$ C. and $-30°$ C., preferably 0° C. and $-10°$ C. Substitution takes place in about 5 to 30 minutes, depending on the starting material employed and the reaction conditions. The product of the reaction is preferably isolated by pouring the reaction mixture onto ice water, rendering the solution alkaline with ammonia or a sodium bicarbonate solution, which is then extracted with a water-immiscible organic solvent, preferably chloroform. The product obtained by evaporation of the chloroform solution may be purified by crystallization or chromatography, and the isomers formed are separated.

The subsequent alkylation of the indole nitrogen in the indolo[2,3-a]quinolizine derivatives of the formula (I) is preferably carried out through the anion prepared in liquid ammonia with sodium amide. In liquid ammonia sodium amide is prepared by means of sodium metal, in a conventional manner, whereupon the indolo[2,3-a]quinolizine derivative to be alkylated is added to the sodium amide obtained, preferably as a solution in tetrahydrofuran. The anion formation is complete in about 2 to 3 hours, whereupon the alkylating agent, preferably alkyl halide, such as methyl iodide is added. The alkylation is terminated in about one hour. The product is preferably isolated by letting the ammonia evaporate, dissolving the residue in a water-immiscible inert organic solvent, preferably chloroform, and evaporating the solution, after washing with water and drying. The crude product obtained may be purified by recrystallization or chromatography.

The subsequent alkylation of the 1-carbon atom of the indolo[2,3-a]quinolizine derivatives of the formula (I) is preferably carried out by the alkylation of the anion generated by means of lithium diisopropyl amide. If the indole nitrogen is unsubstituted, it is also alkylated in this reaction step. If this side-reaction is to be avoided, the indole nitrogen should be protected by a suitable protecting group, preferably by a benzyl group. The best solution for this is to start from tryptamine derivatives of the formula (II), substituted with benzyl.

The additional step of alkylation is preferably carried out by adding to a solution of diisopropyl amine in dry tetrahydrofuran, butyl lithium, hexamethylphosphoric triamide and the indolo[2,3-a]quinolizine derivative of the formula (I), at a temperature of $-30°$ C. to $-70°$ C. and subsequently adding the desired alkylating agent, e.g. ethyl iodide at $0°$ C. Under these conditions the alkylation is complete in about 30 minutes. The product is isolated from the reaction mixture after adding a sodium chloride solution, in a conventional manner, e.g. by extraction, evaporation and subsequent recrystallization or purification by chromatography.

The eventual protecting group attached to the indole nitrogen of the compounds of the formula (I), such as the benzyl group is eliminated by catalytic hydrogenation or by sodium metal in liquid ammonia. Preferably, the indolo[2,3-a]quinolizine derivative of the formula (I) is dissolved in a lower alcohol, preferably having from 1 to 6 carbon atoms, e.g. ethanol or in a cyclic ether, e.g. tetrahydrofuran, a palladium-on-charcoal catalyst is added to the solution, and the mixture is shaken with hydrogen. After splitting off the protecting group, the catalyst is eliminated in a suitable manner, for example by filtration, and the product is isolated from the solution by evaporation. If desired, the product can be purified by recrystallization from an aliphatic, acyclic or aromatic hydrocarbon or a mixture of such solvents, preferably from petroleum ether.

If desired, the racemic indolo[2,3-a]quinolizine derivatives of the formula (I) obtained by the process according to the invention may be separated into their optical isomers. During the resolution generally an acid addition salt of an indolo[2,3-a]quinolizine derivative of the formula (I) with an optically active acid is separated into a mixture of diastereomers by crystallization. As an optically active acid for example tartaric acid, diacyl tartaric acid or a semidialkyl amide of the latter compound, e.g. dibenzoyl(+)-tartaric acid semidimethyl amide, malic acid, camphenic acid or the substituted derivatives of the latter one, etc. can be used. Typical solvents include lower aliphatic alcohols, preferably having from 1 to 6 carbon atoms. If both antipodes of a compound of the formula (I) are to be prepared by resolution, from the salt resulted by the evaporation of the mother liquor obtained after seperation of one of the two isomers, the base enriched in the other antipode is deliberated, and the other antipode is isolated by further resolution with a resolving agent, preferably with the antipode of the resolving agent used in the first step. From the diastereomeric salt pair obtained, if desired, the optically active indolo[2,3-a]quinolizine derivatives of the formula (I) may be set free. For this purpose the salt is dissolved or suspended in a mixture of water and a water-immiscible organic solvent, such as an optionally halogenated aliphatic or aromatic hydrocarbon, a straight-chained or cyclic ether, e.g. dichloromethane, chloroform, ether, toluene, preferably dichloromethane, the solution or suspension is rendered alkaline with an inorganic base, such as ammonia, sodium carbonate, potassium carbonate, preferably sodium carbonate, and the optically active base is extracted with the water-immiscible solvent employed. The pure optically active indolo[2,3-a]quinolizine base of the formula (I) is isolated from the solution e.g. by evaporation and if desired, by subsequent recrystallization.

The resolution of the indolo[2,3-a]quinolizine derivatives of the formula (I) may be carried out also before or after any of the additional substitution steps described hereinabove.

The compounds of the formula (I) may, if desired, be converted into their acid addition salts, preferably pharmaceutically acceptable acid addition salts by reaction with an inorganic or organic acid. Such acids include, amongst others, mineral acids such as, for example hydrohalic acids (e.g. hydrochloric and hydrobromic acids), sulfuric acid and phosphoric acid; organic carboxylic acids such as for example formic acid, acetic acid, propionic acid, glycolic acid, maleic acid, fumaric acid, succinic acid, tartaric acid, ascorbic acid, citric acid, cinnamic acid, benzoic acid, malic acid, lactic acid, asparaginic acid, glutamic acid; methanesulfonic acid, ethanesulfonic acid, p-toluene-sulfonic acid, etc.

Salt formation can be carried out, for example, in an inert organic solvent such as a lower, preferably $C_{1-6}$ aliphatic alcohol, e.g. methyl, ethyl, n-propyl or isopropyl alcohol; in ethers such as ethyl ether, diisopropyl ether; cyclic ethers, e.g. dioxane, tetrahydrofuran or in other inert solvents such as ethyl acetate, acetone or in a mixture of one or more of these solvents, so that the compound of the formula (I) is dissolved in the solvent or solvent mixture, and a calculated amount of the selected acid or a solution thereof formed with the same solvent is added to the first solution, preferably under cooling and stirring. Alternatively, to the solution of the compound of the formula (I) in any of the above solvents or in a mixture thereof the selected acid or a solution thereof formed with the same solvent is added until it becomes slightly acidic (pH ~ 5 to 6). Thereafter the acid addition salt separates out and may be removed from the reaction mixture e.g. by filtration. If desired, the isolated product may be further purified by recrystallization from any of the above solvents or from a suitable mixture thereof.

The vasodilating activity of the compounds of the formula (I) was tested on anaesthesized dogs. On the femoral and internal carotid arteries of the animals electromagnetic rheometers (Hellige) were placed, and the blood flows were measured in ml./min. The arterial mean pressure was measured by a Statham pressure sensor attached to a polyethylene cannula introduced into the artery. The pulse number per minute was determined from the pulsatoric component of the blood pressure by a frequency meter. All the measured parameters were continuously registered on a multichannel polygraph.

The activity of each compound was tested on more animals. The individual data obtained were averaged. In the following tables the number of the animals (n), the mean values of the measured parameters and the %-age changes are indicated. In case of intravenous (i.v.) administration the starting basic values and the maximum change were registered.

In the tests particularly the compound prepared according to Example 1 showed an outstanding biological activity. The results obtained are set forth in Table 1 below.

TABLE 1

The pharmacological activities of the compound prepared according to Example 1—1 mg./kg. i.v. dose (n = 3)

|  | basic | maximum change | duration of activity (min.) |
|---|---|---|---|
| Blood flow in femoral artery | | | |
| ml · min$^{-1}$ | 38 | 87 | 12.7 |
| % | — | +128 | — |
| Blood flow in internal carotid artery | | | |
| ml · min$^{-1}$ | 41 | 36 | 2.3 |
| % | — | −12 | — |
| Blood flow in internal carotis artery | | | |
| kPa | 17.5 | 13.3 | 11.7 |
| % | — | −24 | — |
| Pulse number | | | |
| min$^{-1}$ | 158 | 172 | 3 |
| % | — | +8.8 | — |

The results show that the test compound substantially increases the blood flow in the femoral artery (128%). In other blood vessels, for example in the cerebral region (internal carotis) this effect is absent. The increase in the blood flow is accompanied with a simultaneous reduction in blood pressure, which results in a very high (almost 70%) reduction of the vascular resistance, i.e. in a vasodilation in the femoral region. (Vascular resistance=mean arterial pressure: blood flow). The reduction of the vascular resistance is only 13% in the carotis region, which shows that the compound has a very specific peripheral vasodilating activity.

For comparison the activity of pentoxifylline, a peripheral vasodilator, widely used in therapy, was tested. The results are shown in Table 2.

TABLE 2

Change in the blood flow in the femoral artery 1 mg./kg. i.v. dose of pentoxifylline (n = 5)

|  | basic | maximum change | duration of activity (min.) |
|---|---|---|---|
| ml · min$^{-1}$ | 32.4 | 33.4 | 1.8 |
| % | — | +3.1 | — |

From the data set forth in Tables 1 and 2 it can be concluded that the vasodilating activity of the compounds according to the invention, in particular of the compound prepared according to Example 1 is about two orders of magnitude higher than that of pentoxifylline determined under the same conditions.

Accordingly, the compounds of the formula (I) can be advantageously used in therapy, particularly for the treatment of vasoconstriction. In case of parenteral administration their expected dose is 0.1 to 1.0 mg./kg. of body weight, while in oral administration 1 to 10 mg./kg. of body weight.

The new compounds of the formula (I) and their physiologically acceptable acid addition salts may be formulated for therapeutic purposes. The invention therefore relates also to pharmaceutical compositions comprising as active ingredient at least one compound of formula (I) or a physiologically acceptable acid addition salt thereof, in association with pharmaceutical carriers and/or excipients. Carriers conventional for this purpose and suitable for parenteral or enteral administration as well as other additives may be used. As carriers solid or liquid compounds, for example water, gelatine, lactose, starch, pectine, magnesium stearate, stearic acid, talc, vegetable oils, such as peanut oil, olive oil, etc. can be used. The compounds can be formulated as conventional pharmaceutical formulations, for example in a solid (globular and angular pills, dragées, capsules, e.g. hard gelatine capsules) or liquid (e.g. oily or aqueous solutions, suspensions, emulsions, syrups, soft gelatine capsules, injectable oily or aqueous solutions or suspensions, etc.) form. The quantity of the solid carrier may be varied within wide ranges, but preferably is between 25 mg. and 1 g. The compositions optionally contain also conventional pharmaceutical additives, such as preserving agents, stabilizators, wetting agents, emulsifying agents, salts for adjusting the osmotic pressure, buffers, flavoring and aroma substances, etc.

The compositions according to the invention optionally contain the compounds of formula (I) in association with other known active ingredients. The unit doses are selected depending on the route of administration. The pharmaceutical compositions are prepared by conventional techniques including sieving, mixing, granulation, pressing or dissolution of the ingredients. The formulations obtained may then be subjected to additional conventional treatments, such as sterilization.

The invention is elucidated in detail by the aid of the following non-limiting Examples.

EXAMPLE 1

(±)-Ethyl 12bβ-methyl-1,2,3,4,6,7,12,12b-octahydroindolo[2,3-a]quinolizine-1β-carboxylate hydrochloride To a solution of 20.7 g. (0.1 mole) of (±)-ethyl 2-(3-chloropropyl)-acetoacetate (Cs. Szántay et al: Synthesis, 354, (1974)) in 200 ml. of chlorobenzene 33.6 g. (0.21 mole) of tryptamine are added, whereupon the reaction mixture is boiled for 30 minutes under stirring, allowing the chlorobenzene to distill off slowly. After cooling, the precipitated tryptamine hydrochloride is filtered off, washed with two 15-ml. portions of chlorobenzene, and the combined chlorobenzene solution is evaporated on a rotating evaporator, on a bath of 45° C. and dried in vacuum for two hours. The residue is dissolved in a mixture of 150 ml. of dry dioxane and 150 ml. of dry ethanol, 50 ml. (0.31 mole) of a 6.2 molar solution of hydrochloric acid in dioxane are added to the solution, which is then refluxed for 8 hours, with stirring. After standing overnight the crystalline product is filtered off, washed with three 15-ml. portions of a 4:3 mixture of dry dioxane and dry ethanol and dried.

Yield: 22.7 g. (65%)

Melting point 222° C. to 228° C.

R$_f$: 0.57 (Polygram SIL G/UV$_{254}$, toluene containing 5% of diethyl amine, u.v. light)

Analysis for C$_{19}$H$_{25}$ClN$_2$O$_2$ (348.86): calculated: C 65.41; H 7.22; N 8.03; Cl$_{ionic}$ 10.16%; found C 64.99; H 7.32; N 8.43; Cl$_{ionic}$ 9.81%.

EXAMPLE 2

(±)-Ethyl 12bβ-methyl-1,2,3,4,6,7,12,12b-octahydroindolo[2,3-a]quinolizine-1β-carboxylate 10.46 g. (0.03 mole) of (±)-ethyl 12bβ-methyl-1,2,3,4,6,7,12,12b-octahydroindolo[2,3-a]quinolizine-1β-carboxylate hydrochloride prepared according to Example 1 are suspended in a mixture of 150 ml. of water and 150 ml. of dichloromethane, whereupon the solution is rendered alkaline with 4.8 g. (0.045 mole) of sodium carbonate, under vigorous stirring. When the dissolution of the material is complete, the mixture is separated, the aqueous phase is washed with two 30-ml. portions of dichloromethane, whereupon the combined dichloromethane solution is washed with three 30-ml. portions of water, dried over solid anhydrous magnesium sulfate and evaporated.

Yield: 8.55 g. (91%) - oil crystallizing upon standing
Melting point: 102° C. to 106° C.

EXAMPLE 3

(±)-Ethyl 12bα-methyl-1,2,3,4,6,7,12,12b-octahydroindolo[2,3-a]quinolizine-1β-carboxylate The dioxane/ethanolic mother liquor obtained during the preparation of (±)-ethyl 12bβ-methyl-1,2,3,4,6,7,12,12b-octahydroindolo[2,3-a]quinolizine-1β-carboxylate hydrochloride prepared in Example 1 is evaporated, the residue is dissolved in 250 ml. of water, the solution is carefully rendered alkaline with 13.5 g. (0.127 mole) of sodium carbonate and extracted with three 50-ml. portions of dichloromethane. The combined dichloromethane solution is washed with three 25-ml. portions of water, dried over anhydrous magnesium sulfate and the residue (7.7 g.) is chromatographed on silica gel (500 g., Geduran Si 60, 0.063–0.200 mm.) with toluene containing 5% of diethyl amine.

Yield: 1.50 g. (4.8%) - thick oil
$R_f$: 0.51 (Polygram SIL G/UV$_{254}$, toluene containing 5% of diethyl amine, u.v. light)

EXAMPLE 4

(±)-Ethyl 1-[2-(3-indolyl)-ethyl[-2-methyl-1,4,5,6-tetrahydronicotinate

To a solution of 2.07 g. (0.01 mole) of (±)-ethyl 2-(3-chloropropyl)-acetoacetate in 20 ml. of chlorobenzene 3.36 g. (0.021 mole) of tryptamine are added, and the reaction mixture is boiled for 30 minutes, under stirring, to allow the chlorobenzene to distill off slowly. After cooling the tryptamine hydrochloride separated out is filtered off, washed with a small amount of chlorobenzene twice, and the combined chlorobenzene solution is evaporated on a rotating evaporator, on a bath of 45° C. The thick oily residue is chromatographed on 180 g. of silica gel (Geduran Si 60, 0.063–0.200 mm.) with toluene containing 10% of diethyl amine to yield the pure product.

Yield: 2.20 g. (70%) of an oily product which crystallizes upon standing
Melting point: 93° C. to 97° C.
$R_f$: 0.46 (Polygram SIL G/UV$_{254}$, toluene containing 10% of diethyl amine, u.v. light)
Analysis for $C_{19}H_{24}N_2O_2$ (312.40): calculated: C 73.05; H 7.74; N 8.97%; found: C 72.72; H 8.02; N 8.80%.

EXAMPLE 5

(±)-Ethyl 12bβ-methyl-1,2,3,4,6,7,12,12b-octahydroindolo[2,3-a]quinolizine-1β-carboxylate To a solution of 0.156 g. (0.0005 moles) of ethyl 1-[α-(3-indolyl)-ethyl]-2-methyl-1,4,5,6-tetrahydronicotinate prepared according to Example 4 in 2 ml. of dry dioxane and 2 ml. of dry ethanol 0.25 ml. (0.0015 mole) of a 6.2 molar solution of hydrochloric acid in dioxane are added, and the solution is refluxed with stirring for 7 hours. The solution is evaporated on a rotating evaporator, the residue is dissolved in 10 ml. of water, rendered alkaline with 0.53 g. (0.005 mole) of sodium carbonate and extracted with three 5-ml. portions of dichloromethane. The dichloromethane solution is washed with three 3-ml. portions of water, dried over solid anhydrous magnesium sulfate and evaporated. The residue is chromatographed on 20 g. of silica gel (Geduran Si 60, 0.063 to 0.200 mm.) with toluene containing 5% of diethyl amine, to yield the pure product.

Yield: 0.080 g. (51%)
Melting point: 100° C. to 104° C.
$R_f$: 0.57 (Polygram SIL G/UV$_{254}$, toluene containing 5% of diethyl amine, u.v. light)

EXAMPLE 6

(+)-Dibenzoyl-L-tartaric acid semidimethyl amide 136.0 g. (0.4 mole) of (−)-dibenzoyl-L-tartaric acid anhydride [M. Semonsky et al: Collect., 21, 382 (1956)]are dissolved in a mixture of 112.5 ml (1.0 mole) of a 40% aqueous dimethyl amine solution and 116 ml. of water under slight heating. The solution is allowed to cool and acidified with 42 ml. of concentrated hydrochloric acid. The product solidifying upon trituration is washed with five 125-ml. portions of water, dissolved in 450 ml. of ethanol and the solution is diluted with 450 ml. of water. The crystalline product is filtered off, washed with 50% aqueous ethanol and dried at 100° C.

Yield: 115.6 g. (75%)
Melting point: 149° C. to 152° C. $[\alpha]_D^{22} = +76.5°$ (c=2.0, ethanol).

Literature (König R., Földi Z.: Hungarian Patent Specification No. 146,896) data for the (−) form:
melting point: 150° C., $[\alpha]_D^{20} = -76°$ (ethanol).

EXAMPLE 7

Resolution of (±)-ethyl 12bβ-methyl-1,2,3,5,6,7,12,12b-octahydroindolo-[2,3-a]quinolizine-1β-carboxylate A solution of 19.37 g. (0.062 mole) of (±)-ethyl 12bβ-methyl-1,2,3,4,6,7,12,12b-octahydroindolo[2,3-a]quinolizine-1β-carboxylate (Example 2) in 200 ml. of dry methanol is added to the solution of 23.87 g. (0.062 mole) of (−)-dibenzoyl-D-tartaric acid semidimethyl amide (König R., Földi Z.: Hungarian Patent Specification No. 146,896) in 240 ml. of dry methanol.

In several hours the product separates out in a crystalline form and is filtered off after standing overnight. It is then washed with three 15-ml. portions of ethanol and dried over phosphorus (V) oxide at room temperature.

Yield: 17.11 g. (39.6%) of the salt of (−)-base with the (−)-acid
Melting point: 110° C. to 112° C. $[\alpha]_D^{22} = -43.7°$ (c=2; acetone)

After recrystallization from methanol the melting point and specific rotatory power remain the same. By evaporation of the mother liquor to 150 ml. a further 2.03 g. portion of the product may be obtained, having the same melting point and specific rotatory power. Accordingly, the total yield is 44.3%.

To a solution of 18.47 g. (0.0265 mole) of the above (−)-salt in a mixture of 150 ml. of water and 150 ml. of dichlormethane 4.21 g. (0.0397 mole) of sodium carbonate are added and the mixture is vigorously stirred for 30 minutes. After separation the aqueous phase is washed with two 25-ml. portions of dichloromethane, the combined dichloromethane solution is washed with three 25-ml. portions of water, dried over solid, anhydrous magnesium sulfate and evaporated.

Yield: 8.11 g. (98%; 43.4% calculated for the starting ($\pm$)-base, ($-$)-base, thick oil $[\alpha]_D^{22} = -42.0°$ (c=2.1; ethanol)

The above resolution mother liquor is evaporated, the residue (27.2 g.) is dissolved in 200 ml. of dichloromethane. Thereafter 200 ml. of water are added to the solution, followed by the addition of 6.36 g. (0.060 mole) of sodium carbonate under vigorous stirring, and the mixture is intensively stirred for additional 30 minutes. The phases are separated, and the aqueous phase is washed with two 30-ml. portions of dichloromethane and the combined dichloromethane solution with three 30-ml. portions of water. The solution is then dried over solid anhydrous magnesium sulfate and evaporated. The residue (base enriched in the (+)-form, 10.35 g., 0.0332 mole, $[\alpha]_D^{25} = +34.9°$, c=2; ethanol) is dissolved in 100 ml. of dry methanol. The solution is added to a solution of 12.77 g. (0.0332 mole) of (+)-dibenzoyl-L-tartaric acid semidimethyl amide prepared according to Example 6 in 120 ml. of dry methanol and the precipitated material is dissolved by bringing the solution up to the boil. Upon cooling the product separates out in a crystalline form. After standing for 6 hours the product is filtered off, washed with three 20-ml. portions of dry methanol and subsequently dried over phosphorus(V)-oxide at room temperature.

Yield: 16.58 g. (38.4%) of the salt of the (+)-base with the (+)-acid

Melting point: 110° C. to 112° C. $[\alpha]_D^{22} = +44.8°$ (c=2.0; acetone)

16.27 g. (0.0233 mole) of the above (+)-salt are dissolved in 150 ml. of dichloromethane, the solution is supplemented with 150 ml. of water and subsequently with 3.71 g. (0.035 mole) of sodium carbonate, under vigorous stirring, and the mixture is intensively stirred for another 30 minutes. The phases are separated, and the aqueous phase is washed with two 25-ml. portions of dichloromethane. The dichloromethane solutions are combined and then washed with three 25-ml. portions of water, dried over solid anhydrous magnesium sulfate and evaporated.

Yield: 7.22 g. (99%, 38.0% related to the starting ($\pm$)-base) of (+)-base, thick oil $[\alpha]_D^{26} = +43.1°$ (c=2.0; ethanol)

EXAMPLE 8

($\pm$)-Ethyl 2-(3-bromopropyl)-2-ethyl-acetoacetate ester 12.87 g. (0.065 mole) of ($\pm$)-ethyl 2-allyl-2-ethyl-acetoacetate (A. C. Cope et al: J. Am. Chem. Soc., 63, 1843 (1949)) are dissolved in 13 ml. of dry toluene, whereupon 0.040 g. of benzoyl peroxide are added to the solution, followed by the inlet of hydrogen bromide gas under ice cooling, until saturation. The mixture is poured onto 25 ml. of ice, after the ice is melted the phases are separated, and the toluene solution is washed subsequently with two 15-ml. portions of water, 5% aqueous sodium bicarbonate solution and water, respectively, dried over anhydrous magnesium sulfate and evaporated. The residue is distilled by fractionation in vacuum in a short Vigreux column.

Yield: 1.82 g. (10%)

Boiling point: 121° C. to 122° C./1 mmHg.

EXAMPLE 9

($\pm$)-Ethyl 1$\beta$-ethyl-12b$\beta$-methyl-1,2,3,4,6,7,12,12b-octahydroindolo[2,3-a]quinolizine-1$\alpha$-carboxylate To a solution of 1.162 g. (0.00416 mole) of ($\pm$)-ethyl 2-(3-bromopropyl)-2-ethyl-acetoacetate prepared according to Example 8 in 17 ml. of chlorobenzene 1.333 g. (0.00832 mole) of tryptamine are added, and the mixture is slightly boiled for 12 hours, under stirring, allowing the chlorobenzene to distill off slowly. The precipitated tryptamine hydrobromide is filtered off, washed with chlorobenzene and the combined solution is evaporated on a rotating evaporator. The pure product is obtained by chromatographic purification of the residue (1.67 g.) on 160 g. of silica gel (Geduran Si 60, 0.063-0.200 mm.) with toluene containing 10% of diethyl amine.

Yield: 0.151 g. (10.7%) of an oily product which crystallizes upon standing, further purification is possible by crystallization from cyclohexane Melting point: 160° C. to 163° C.

$R_f$: 0.73 (Polygram SIL G/UV$_{254}$, toluene containing 10% of diethyl amine, u.v. light)

EXAMPLE 10

($\pm$)-Ethyl 1$\alpha$-ethyl-12b$\beta$-methyl-1,2,3,4,6,7,12,12b-octahydroindolo[2,3-a]quinolizine-1$\beta$-carboxylate The title compound is obtained by collecting the $R_f$=0.88 fractions during the chromatography of ($\pm$)-ethyl 1$\beta$-ethyl-12b$\beta$-methyl-1,2,3,4,6,7,12,12b-octahydroindolo[2,3-a]quinolizine-1$\alpha$-carboxylate described in Example 9.

Yield: 0.056 g. (4.0%) of an oily product crystallizing upon standing, which can be further purified by crystallization from n-pentane Melting point: 135° C. to 138° C.

$R_f$: 0.88 (Polygram SIL G/UV$_{254}$, toluene containing 10% of diethyl amine, u.v. light)

EXAMPLE 11

Ethyl 1-[2-(1-methyl-indol-3-yl)-ethyl]-2-methyl-1,4,5,6-tetrahydronicotinate 5.0 g. (0.0287 mole) of N-methyl-triptamine (K. T. Potts, J. E. Saxton: J. Chem. Soc., 2641 (1954)) and 4.77 ml. of triethyl amine dried on potassium hydroxide are added to a solution of 5.948 g. (0.0287 mole) of ($\pm$) ethyl 2-(3-chloropropyl)-acetoacetate in 60 ml. of chlorobenzene, and the mixture obtained is kept at 150° C. for two hours. After cooling to room temperature the precipitated triethyl amine hydrochloride is filtered off, the filtrate is evaporated on a rotating evaporator and the crude product is purified by column chromatography on silica gel (500 g. of Geduran Si 60; 0.063-0.200 mm.) in cyclohexane containing 10% of diethyl amine.

Yield: 5.2 g. (55.5%) of the title compound, which can be further purified by recrystallization from n-hexane or isopropyl alcohol.

Melting point: 97° C. to 99° C.

$R_f$: 0.33 (Polygram SIL g/UV$_{254}$, cyclohexane containing 10% of diethyl amine, u.v. light)

EXAMPLE 12

(±)-Ethyl 12,12bβ-dimethyl-1,2,3,4,6,7,12,12b-octahydroindolo[2,3-a]quinolizine-1β-carboxylate 0.820 g. (0.0025 mole) of ethyl 1-[2-(1-methyl-indol-3-yl)-ethyl]-2-methyl-1,4,5,6-tetrahydronicotinate prepared according to Example 11 are dissolved in a mixture of 10 ml. of dry dioxane and 2.5 ml. of dry ethanol, and the solution is kept at 100° C. for 45 hours, in the presence of 1.25 ml. (0.00835 mole) of a 6.68 molar solution of hydrochloric acid in dioxane. The reaction mixture is evaporated, the residue is dissolved in 20 ml. of dichlormethane, 15 ml. of water are added to the solution, which is then rendered alkaline with a 10% aqueous sodium carbonate solution. After separation of the phases the aqueous part is washed with two 10-ml. portions of dichloromethane, and the combined dichloromethane solution is dried over solid anhydrous magnesium sulfate, evaporated and the product is purified by chromatography on a silica gel column (60 g. of Geduran Si 60, 0.063–0.200 mm.) using dichloromethane containing 5% of diethyl amine and 5% of isopropanol as an eluting agent.

Yield: 0.019 g. (2.3%) of an oily product

EXAMPLE 13

Bromination of (±)-ethyl 12bβ-methyl-1,2,3,4,6,7,12,12b-octahydroindolo[2,3-a]quinolizine-1β-carboxylate 9.372 g. (0.03 mole) of (±)-ethyl 12bβ-methyl-1,2,3,4,6,7,12,12b-octahydroindolo[2,3-a]quinolizine-1β-carboxylate prepared according to Example 2 are dissolved in 80 ml. of trifluoroacetic acid, 7.087 g. (0.0396 mole) of N-bromo-succinimide are added to the solution under stirring, and the mixture is stirred for further 4 hours at room temperature, while the reaction is monitored by thin layer chromatography (Polygram SIL G/UV$_{254}$, petroleum ether containing 10% of diethyl amine, u.v. light). When the starting material is completely used up, the reaction mixture is rendered alkaline with 320 ml. of a 20% aqueous sodium carbonate solution, whereupon it is extracted with three 100-ml. portions of chloroform, the chloroform extract is washed with two 50-ml. portions of water, dried over anhydrous magnesium sulfate and evaporated to dryness on a rotating evaporator. The obtained crude pulp is crystallized from petroleum ether two subsequent times.

(±)-Ethyl 9-bromo-12bβ-methyl-1,2,3,4,6,7,12,12b-octahydroindolo[2,3-a]quinolizine-1β-carboxylate Yield: 2.5 g. (21.3%)

Melting point: 128° C. to 130° C.

R$_f$: 0.45

The mother liquors of recrystallization are evaporated and by chromatography of the residue on silica gel, with petroleum ether containing 20% of diethyl amine, in addition to the above product, the following compounds are isolated.

(±)-Ethyl 10-bromo-12bβ-methyl-1,2,3,4,6,7,12,12b-octahydroindolo[2,3-a]quinolizine-1β-carboxylate Yield: 0.5 g. (4.2%)

Melting point: 104° C. to 105° C.

R$_f$: 0.51

(±)-Ethyl 8,9-dibromo-12bβ-methyl-1,2,3,4,6,7,12,12b-octahydroindolo[2,3-a]quinolizine-1β-carboxylate Yield: 0.15 g. (1.06%) of a glassy product R$_f$: 0.37

Thin layer chromatography was carried out in case of all three products under the following conditions: Polygram SIL G/UV$_{254}$, petroleum ether containing 20% of diethyl amine, u.v. light.

EXAMPLE 14

Nitration of (±)-ethyl 12bβ-methyl-1,2,3,4,6,7,12,12b-octahydroindolo[2,3-a]quinolizine-1β-carboxylate 3.12 g. (0.01 mole) of (±)-ethyl 12β-methyl-1,2,3,4,6,7,12,12b-octahydroindolo[2,3-a]quinolizine-1β-carboxylate prepared according to Example 2 are dissolved in 18 ml. of dry acetic acid, and the solution is added dropwise to a mixture of 5.4 ml. of dry acetic acid and 5.4 ml. of 100% nitric acid at 0° C. to −10° C., taking care that the internal temperature should not exceed 0° C. After stirring the mixture for another 5 minutes it is poured onto 200 ml. of ice water, the solution is acidified with a 25% aqueous ammonia solution, extracted with chloroform, the organic phase is washed with water, dried over solid anhydrous magnesium sulfate and is evaporated to dryness. The crude product obtained is purified by column chromatography carried out on silica gel (300 g. of Geduran Si 60, 0.063–0.200 mm.) with tetrachloromethane containing 10% of diethyl amine and is then separated into its components. The following products are obtained:

(±)-ethyl 12bβ-methyl-10-nitro-1,2,3,4,6,7,12,12b-octahydroindolo[2,3-a]quinolizine-1β-carboxylate:

Yield: 1.38 g. (38.6%);

Melting point: 136° to 138° C. (crystallization from dry ethanol);

R$_f$: 0.50.

(±)-ethyl 12bβ-methyl-8-nitro-1,2,3,4,6,7,12,12b-octahydroindolo[2,3-a]quinolizine-1β-carboxylate:

Yield: 0.88 g. (24.6%);

melting point: 128° C. to 130° C. (crystallization from dry ethanol);

R$_f$: 0.43.

(±)-ethyl-12bβ-methyl-8,10-dinitro-1,2,3,4,6,7,12,12b-octahydroindolo[2,3-a]quinolizine-1β-carboxylate Yield: 0.18 g. (4.5%);

Melting point: 215° C. to 218° C.;

R$_f$: 0.26.

Thin layer chromatography was carried out in case of all three compounds on Polygram SIL G/UV$_{254}$, with tetrachloromethane containing 10% of diethyl amine, under u.v. illumination.

EXAMPLE 15

(±)-Ethyl 12,12bβ-dimethyl-1,2,3,4,6,7,12,12b-octahydroindolo[2,3-a]quinolizine-1β-carboxylate Into 50 to 60 ml. of liquid ammonia there are added a catalytic amount of a 1:9 mixture of ferric(III)nitrate and water and subsequently, portionwise 0.77 g. (0.033 mole) of sodium metal, both at −70° C., under vigorous stirring. After dissolution of sodium, disappearance of the blue color and the precipitation of the grey sodium amide a solution of 3.12 g. (0.01 mole) of (±)-ethyl 12bβ-methyl-1,2,3,4,6,7,12,12b-octahydroindolo[2,3-a]quinolizine-1β-carboxylate prepared according to Example 2 in 100 ml. of dry tetrahydrofurane is added to the mixture dropwise, at −60° C. After stirring for 3 hours, while the internal temperature increases up to −40° C., the reaction mixture is cooled to −50° C., 3.5 g. (0.025 mole) of methyl iodide are added dropwise to the mixture, which is then stirred until the internal temperature becomes again −40° C. Thereafter the cooling bath is removed and the ammonia is allowed to evaporate. The residual solution is evaporated, the residue is dissolved in 300 ml. of chloroform, washed with three 150-ml. portions of water, dried over anhydrous magnesium sulfate and evaporated. The solid residue is purified by chromatography of 250 g. of silica gel (Geduran Si 60, 0.063–0.200 mm.) using toluene containing 10% of diethyl amine as an eluting agent.

Yield: 2.6 g. (79.8%) of a pale yellow oil, $R_f$: 0.38 (Polygram SIL G/UV$_{254}$, petroleum ether containing 10% of diethyl amine, u.v. light).

EXAMPLE 16

(±)-Ethyl 12,12bβ-dimethyl-1,2,3,4,6,7,12,12b-octahydroindolo[2,3-a]quinolizine-1β-carboxylate ethanesulfonate 1.232 g. (0.00377 mole) of the base prepared according to Example 15 are dissolved in 40 ml. of ether. To the solution a solution of 0.415 g. (0.00377 mole) of ethanesulfonic acid in 10 ml. of ether is added dropwise, under ice cooling and stirring. The precipitated salt is filtered off, dried and recrystallized from a mixture of acetone and ether.

Yield: 1.20 g. (73.5%)

Melting point: 172° C. to 175° C.

Analysis for $C_{22}H_{32}N_2O_5S$ (436.57): calculated: C 60.52; H 7.40; N 6.42; S 7.35%; found: C 60.61; H 7.64; N 6.43; S 7.25%.

EXAMPLE 17

(±)-Ethyl 1β-ethyl-12,12bβ-dimethyl-1,2,3,4,6,7,12,12b-octahydroindolo[2,3-a]quinolizine-1α-carboxylate A solution of 1.75 ml. (0.0124 mole) of dry isopropyl amine in 10 ml. of dry tetrahydrofurane is cooled to −50° C. under argon atmosphere, 6.85 ml. (0.011 mole) of a 1.6 molar solution of n-butyl-lithium in n-hexane are added, and the mixture is stirred for 5 minutes at −50° C. and then for 10 minutes at −30° C. It is then cooled to −78° C., there are added 1.85 ml. (0.011 mole) of dry hexamethylphosphoric acid triamide, and the mixture is stirred at this temperature for one hour. Thereafter, a solution of 0.979 g. (0.0003 mole) of (±)-ethyl 12,12bβ-dimethyl-1,2,3,4,6,7,12,12b-octahydroindolo[2,3-a]quinolizine-1β-carboxylate prepared according to Example 15 in 20 ml. of dry tetrahydrofuran is added dropwise, carefully, whereupon the reaction mixture is stirred for 5 minutes at this temperature and then at 0° C. for 10 minutes. After adding 1.04 ml. (0.013 mole) of ethyl iodide the mixture is stirred at 0° C. for further 5 minutes. The outer cooling is terminated, 50 ml. of a 25% aqueous sodium chloride solution are added to the reaction mixture, which is then shaken, the two phases are separated and the aqueous phase is extracted with 30 ml. of ether. The organic phases are combined, dried over solid anhydrous magnesium sulfate and evaporated. The solid residue is purified by chromatography on 100 g. of silica gel (Geduran Si 60, 0.063–0.200 mm.) with petroleum ether containing 10% of diethyl amine, and the crude product is recrystallized from n-hexane.

Yield: 0.242 g. (22.7%)

Melting point: 132° C. to 135° C.

$R_f$: 0.39 (Polygram SIL G/UV$_{254}$, petroleum ether containing 10% of diethyl amine, u.v. light).

Analysis for $C_{22}H_{30}N_2O_2$ (354.48): calculated: C 74.54; H 8.53; N 7.90%; found: C 74.41; H 8.59; N 7.80%.

EXAMPLE 18

(±)-Ethyl 1β-ethyl-12,12bβ-dimethyl-1,2,3,4,6,7,12,12b-octahydroindolo[2,3-a]quinolizine-1α-carboxylate ethanesulfonate 0.570 g. (0.0016 mole) of the base prepared according to Example 17 are dissolved in 100 ml. of ether, whereupon a solution of 0.177 g. (0.0016 mole) of ethanesulfonic acid in 10 ml. of ether is added to the ethereal solution dropwise, under ice cooling and stirring. The precipitated salt is filtered off and dried.

Yield: 0.680 g. (91%) of the title compound, which can be further purified by recrystallization from a mixture of acetone and diisopropyl ether.

Melting point: 198° C. to 201° C.

Analysis for $C_{24}H_{36}N_2O_5S$ (464.61): calculated: C 62.04; H 7.81; N 6.03; S 6.90%; found: C 61.95; H 7.78; N 6.08; S 6.59%.

EXAMPLE 19

(±)-Ethyl 1β,12,12bβ-trimethyl-1,2,3,4,6,7,12,12b-octahydroindolo[2,3-a]quinolizine-1α-carboxylate Into 50 to 60 ml. of liquid ammonia there are added a catalytic amount of a 1:9 mixture of ferric (III) nitrate and water and subsequently, dropwise 0.92 g. (0.04 mole) of sodium metal, both at −70° C., under vigorous stirring. After dissolution of sodium, disappearance of the blue color and precipitation of the grey sodium amide a solution of 3.12 g. (0.01 mole) of (±)-ethyl 12bβ-methyl-1,2,3,4,6,7,12,12b-octahydroindolo[2,3-a]quinolizine-1β-carboxylate prepared according to Example 2 in 100 ml. of dry tetrahydrofuran is added dropwise, at −60° C. After stirring for 3 hours, when the internal temperature increases up to −40° C., the reaction mixture is cooled to −50° C. There are added 5.67 g. (0.04 mole) of methyl iodide dropwise, and the mixture is stirred until the internal temperature increases again up to −40° C. (about 2 hours). Thereafter the external bath is removed and the ammonia is allowed to evaporate. The residual solution is evaporated, the residue is dissolved in 300 ml. of chloroform, washed with three 150-ml. portions of water, dried over solid anhydrous magnesium sulfate and evaporated. The residue is purified by chromatography on 250 g. of silica gel (Geduran Si 60, 0.063–0.200 mm.), using petroleum ether containing 10% of diethyl amine as an eluting agent.

Yield: 0.377 g. (11%)

Melting point: 124° C. to 125° C.

$R_f$: 0.55 (Polygram SIL G/UV$_{254}$, petroleum ether containing 10% of diethyl amine, u.v. light).

EXAMPLE 20

(±)-Ethyl 2-acetyl-2-ethyl-5-[2-(3-indolyl)-ethyl]-amino-valerate 0.160 g. (0.001 mole) of tryptamine are added to a solution of 0.140 g. (0.0005 mole) of (±)-ethyl 2-(3-bromopropyl)-2-ethyl-acetoacetate prepared according to Example 8 in 2 ml. of chlorobenzene, and the solution is refluxed for 45 minutes on an oil bath of 150° C., under stirring. After cooling the precipitate is filtered off, washed with chlorobenzene, and the combined chlorobenzene solution is evaporated on a bath of 40° C. The residue is purified by chromatography on 40 g. of silica gel (Geduran Si 60, 0.063–0.200 mm.), using toluene containing 5% of diethyl amine for the elution.

Yield: 0.076 g. (42%), slowly solidifying oil, $R_f$: 0.23 (Polygram SIL G/UV$_{254}$, toluene containing 5% of diethyl amine, u.v. light).

EXAMPLE 21

5-Acetyl-6-methyl-3,4-dihydro-2H-pyrane

A mixture of 130.4 g. (1.3 moles) of 2,4-pentanedione, 251.9 g. (1.6 moles) of 1,3-bromochloropropane, 168 g. (1.2 moles) of anhydrous potassium carbonate, 1 g. of anhydrous sodium iodide and 250 ml. of dry acetone is refluxed for 20 hours, under exclusion of humidity, with stirring. After cooling the mixture is filtered, washed with four 150-ml. portions of dry acetone, the combined acetone extract is evaporated, and the residue is subjected to fractionated distillation in vacuum, on a Vigreux column.

Yield: 64.2 g. (35%)

Boiling point: 76° C. to 79° C./2 mmHg. $n_D^{23}$: 1.5040

Analysis for $C_8H_{12}O_2$ (140.18): calculated: C 68.54; H 8.63%; found: C 68.47; H 3.88%.

EXAMPLE 22

3-(3-Bromopropyl)-2,4-pentanedione 35.0 g. (0.25 mole) of 5-acetyl-6-methyl -3,4-dihydro-2H-pyrane prepared according to Example 21 are added dropwise into 250 ml. of a 33% solution of of hydrogen bromide in acetic acid, at room temperature, under stirring. The mixture is refluxed for 4 hours, with stirring. After cooling it is poured into 1 kg. of ice water and is then extracted with three 100-ml. portions of chloroform. The combined chloroform solution is washed subsequently with three 50-ml. portions of water, three 50-ml. portions of a 5% aqueous sodium bicarbonate solution and two 50-ml. portions of water, dried over solid anhydrous magnesium sulfate, decoloured with activated carbon and evaporated. The product obtained is purified by fractionated distillation on a short Wigreux column, in vacuum.

Yield: 40.3 g. (73%)

Boiling point: 115° C. to 119° C./2 mmHg $n_D^{23}$: 1.4996

Analysis for $C_8H_{13}BrO_2$ (221.09): calculated: C 43.46; H 5.93; Br 36.14%; found: C 44.14; H 6.31; Br 36.29%.

EXAMPLE 23

3-Acetyl-1-[2-(3-indolyl)-ethyl]-2-methyl-1,4,5,6-tetrahydropyridine 2.21 g. (0.01 mole) of 3-(3-bromopropyl)-2,4-pentanedione prepared according to Example 22 are dissolved in 50 ml. of chlorobenzene, 3.20 g. (0.02 mole) of tryptamine are added to the solution, which is then boiled on an oil bath of 150° C. for 10 minutes, with stirring, letting the water formed distill off together with the chlorobenzene. After cooling the precipitate is filtered off, washed with chlorobenzene and the combined chlorobenzene solution is evaporated on a rotating evaporator on a bath of 40° C. The residue is subjected to column chromatography on 220 g. of silica gel (Geduran Si 60, 0.063–0.200 mm.) using toluene containing 10% of diethyl amine for the elution. If desired, the product may be further purified by recrystallization from toluene.

Yield: 1.028 g. (47%)

Melting point: 129° C. to 131° C.

$R_f$: 0.23 (Polygram SIL G/UV$_{254}$, toluene containing 10% of diethyl amine, u.v. light).

Analysis for $C_{18}H_{22}N_2O$ (282.37): calculated: C 76.56; H 7.85; N 9.92%; found: C 76.91; H 8.00; N 9.98%.

EXAMPLE 24

(±)-1β-Acetyl-12bβ-methyl-1,2,3,4,6,7,12,12b-octahydroindolo[2,3-a]quinolizine 0.424 g. (0.0015 mole) of 3-acetyl-1-[2-(3-indolyl)-ethyl]-2-methyl-1,4,5,6-tetrahydropyridine prepared according to Example 23 are dissolved in a mixture of 7.5 ml. of concentrated hydrochloric acid and 7.5 ml. of water, and the solution is allowed to stand at room temperature for two hours. It is then diluted with 30 ml. of water and rendered alkaline with 5.3 g. of sodium carbonate. The precipitated crystalline product is filtered off, washed with water and dried over phosphorus (V) oxide in vacuum. If desired, the product is further purified by recrystallization from n-hexane or aqueous methanol.

Yield: 0.382 g. (90%)

Melting point: 118° C. to 120° C.

$R_f$: 0.64 (Polygram SIL G/UV$_{254}$, 1,2-dichloroethane containing 5% of diethyl amine, u.v. light)

EXAMPLE 25

(±)-1β-Acetyl-12bα-methyl-1,2,3,4,6,7,12,12b-octahydroindolo[2,3-a]quinolizine 0.282 g. (0.001 mole) of 3-acetyl-1-[2-(3-indolyl)-ethyl]-2-methyl-1,4,5,6-tetrahydropyridine prepared according to Example 23 are dissolved in a mixture of 5 ml. of dry ethanol and 5 ml. of dry dioxane. 0.75 ml. (0.005 mole) of a 6.6 molar solution of hydrochloric acid in dry dioxane are added to the solution, whereupon the mixture is refluxed for two hours, under stirring. The solution is evaporated, 10 ml. of dry ethanol are distilled off from the evaporation residue, to the residue 15 ml. of ether and 5 ml. of a 10% sodium carbonate solution are added, and the mixture is carefully shaken. After separation the aqueous phase is extracted with three 10-ml. portions of ether, the combined ethereal solution is washed with 2 ml. of a 10% aqueous sodium carbonate solution and then with two 5-ml. portions of water. It is dried over solid anhydrous magnesium sulfate and evaporated. The residue is purified by chromatography on 80 g. of silica gel (Geduran Si 60, 0.063–0.200 mm.) using cyclohexane containing 20% of diethyl amine as an eluent. The pure product is accompanied with the corresponding 12bβ-methyl epimer (0.039 g., 14%, $R_f$: 0.64).

Yield: 0.049 g. (17%) of an oily product solidifying upon standing $R_f$: 0.51 (Polygram SIL G/UV$_{254}$, 1,2-dichloroethane containing 5% of diethyl amine, u.v. light).

EXAMPLE 26

(±)-1-Phenyl-2-(3-chloropropyl)-1,3-butanedione 0.81 g. (0.005 mole) of 1-phenyl-1,3-butanedione are dissolved in 5 ml. (0.005 mole) of a 1 molar solution of tetrabutyl ammonium fluoride in tetrahydrofuran, whereupon 1.22 g. (0.006 mole) of 1,3-iodochloropropane are added to the solution. After standing for one hour the mixture is diluted with 20 ml. of dry ether, the precipitated substance is filtered off, washed with dry ether and the combined ethereal solution is evaporated. The residue is subjected to chromatography on 90 g. of silica gel (Geduran Si 60, 0.063–0.200 mm.), using cyclohexane containing 30% of diisopropyl ether as an eluent, to yield the title compound as a pure product.

Yield: 0.225 g. (19%) of an oily substance $R_f$: 0.21 (Polygram SIL G/UV$_{254}$, cyclohexane containing 30% of diisopropyl ether, u.v. light).

EXAMPLE 27

3-Benzoyl-1-[2-(3-indolyl)-ethyl]-2-methyl-1,4,5,6-tetrahydropyridine

To a solution of 0.140 g. (0.00059 mole) of (±)-1-phenyl-2-(3-chloropropyl)-1,3-butanedione prepared according to Example 26 in 3 ml. of chlorobenzene 0.188 g. (0.00117 mole) of tryptamine are added, and the reaction mixture is boiled for one hour on an oil bath of 150° C., while the water formed is slowly distilled off together with the chlorobenzene. After cooling the precipitate is filtered off, it is carefully washed with chlorobenzene, dichloromethane and finally with acetone, and the combined solution is evaporated on a rotating evaporator, from a bath of 40° C. The residue is purified by chromatography on 40 g. of silica gel (Geduran Si 60, 0.063–0.200 mm.) using toluene containing 10% of diethyl amine for the elution.

Yield: 0.115 g. (57%)

Melting point: 145° C. to 153° C.

$R_f$: 0.27 (Polygram SIL G/UV$_{254}$, toluene containing 10% of diethyl amine, u.v. light)

EXAMPLE 28

(±)-1β-Benzoyl-12bβ-methyl-1,2,3,4,6,7,12,12b-octahydroindolo[2,3-a]quinolizine 0.185 ml. (0.00122 mole) of a 6.6 molar solution of hydrochloric acid in dry dioxane are added to a solution of 0.084 g. (0.000244 mole) of 3-benzoyl-1-[2-(3-indolyl)-ethyl]-2-methyl-1,4,5,6-tetrahydropyridine prepared according to Example 27 in a mixture of 0.5 ml. of dry ethanol and 0.5 ml. of dry dioxane, and the solution is refluxed for 4 hours. After cooling the solution is evaporated, 10 ml. of dichloromethane and 10 ml. of water are added to the residue, which is then rendered alkaline with sodium carbonate. The phases are separated, and the aqueous phase is washed with 5 ml. of dichloromethane followed by the evaporation of the combined dichloromethane solution. The residue is purified by chromatography on 12 g. of silica gel (Geduran Si 60, 0.063–0.200 mm.) using cyclohexane containing 10% of diethyl amine as an eluent.

Yield: 0.045 g. (54%) of a slowly solidifying oil $R_f$: 0.45 (Polygram SIL G/UV$_{254}$, cyclohexane containing 10% of diethyl amine, u.v. light)

EXAMPLE 29

(+)-Ethyl 2-benzoyl-5-chloro-valerate 25.0 ml. (0.025 mole) of 1 molar solution of tetrabutylammonium fluoride in tetrahydrofurane are added to 4.80 g. (0.025 mole) of ethylbenzoyl acetate, after 30 minutes the solution is poured into 6.10 g. (0.03 mole) of 1,3-iodochloropropane and the mixture is allowed to stand overnight. The material precipitated by adding 100 ml. of dry ether is filtered off, is thoroughly washed with dry ether two subsequent times, and the combined ethereal solution is evaporated. The title compound is obtained by distilling the residue on a short Vigreux column in vacuum. The product may be further purified by chromatography on silica gel using toluene containing 5% of ethyl acetate for the elution.

Yield: 1.89 g. (28%)

Boiling point: 142° C. to 143° C./2 mmHg $R_f$: 0.33 (Polygram SIL G/UV$_{254}$, toluene containing 5% of ethyl acetate)

$n_D^{23}$: 1.5260

EXAMPLE 30

Ethyl 2-phenyl-1-[2-(3-indolyl)-ethyl]-1,4,5,6-tetrahydronicotinate 0.273 g. (0.0017 mole) of tryptamine are added to a solution of 0.229 g. (0.00085 mole) of (±)-ethyl 2-benzoyl-5-chloro-valerate prepared according to Example 29 in 5 ml. of chlorobenzene, and the reaction mixture is heated on an oil bath of 150° C. for 5 hours, with stirring, while the water formed is allowed to distill off slowly together with chlorobenzene. After cooling the precipitate is filtered off, washed with chlorobenzene, and the combined chlorobenzene solution is evaporated from a bath of 40° C. on a rotating evaporator. The title compound is obtained by subjecting the residue to column chromatography on 40 g. of silica gel (Geduran Si 60, 0.063–0.200 mm.) using toluene containing 10% of diethyl amine as an eluting agent.

Yield: 0.167 g. (52%) of a slowly solidifying oil $R_f$: 0.42 (Polygram SIL G/UV$_{254}$, toluene containing 10% of diethyl amine, u.v. light)

EXAMPLE 31

(±)-Ethyl 12bα-phenyl-1,2,3,4,6,7,12,12b-octahydroindolo[2,3-a]quinolizine-1β-carboxylate 0.225 ml. (0.0015 mole) of a 6.6 molar solution of hydrochloric acid in dry dioxane are added to a solution of 0.107 g. (0.000286 mole) of ethyl 2-phenyl-1-[2-(3-indolyl)-ethyl]-1,4,5,6-tetrahydronicotinate in a mixture of 1.5 ml. of dry ethanol and 1.5 ml. of dry dioxane, and the solution is refluxed for 20 hours. After cooling the solution is evaporated, the residue is supplemented with 15 ml. of ether and 5 ml. of a 10% aqueous sodium carbonate solution and thoroughly shaken. The phases are separated and the aqueous solution is washed with two 10-ml. portions of ether. The combined ethereal solution is then washed with 5 ml. of a 10% aqueous sodium carbonate solution and subsequently with two 5-ml. portions of water, dried over solid anhydrous magnesium sulfate and evaporated. The residue is chromatographed on 20 g. of silica gel (Gerduran Si 60, 0.063–0.200 mm.) using cyclohexane containing 10% of diethyl amine as an eluting agent, to yield the aimed compound.

Yield: 0.027 g. (25%) of an oily product solidifying upon standing

Melting point: 140° C. to 146° C.

$R_f$: 0.74 (Polygram SIL G/UV$_{254}$, cyclohexane containing 10% of diethyl amine, u.v. light)

EXAMPLE 32

Ethyl 1-[2-(5-hydroxy-indol-3-yl)-ethyl]-2-methyl-1,4,5,6-tetrahydronicotinate 2.33 g. (0.0132 moles) of 5-hydroxytryptamine and 2.19 ml. (0.0158 moles) of triethyl amine dried over potassium hydroxide are added to a solution of 2.73 g. (0.0132 moles) of (±)-ethyl-2-(3-chloropropyl)-acetoacetate, whereupon the mixture is heated at 150° C. for three hours allowing the chlorobenzene to distill off slowly. After cooling the precipitated triethyl amine hydrochloride is filtered off, the filtrate is evaporated to dryness on a rotating evaporator, and the crude product is purified by chromatography on silica gel (200 g., Geduran Si 60, 0.063–0.200 mm.), using toluene containing 30% of diethyl amine as an eluent.

Yield: 2.2 g. (43%) of an oily product $R_f$: 0.44 (Polygram SIL G/UV$_{254}$, toluene containing 30% of diethyl amine, u.v. light)

EXAMPLE 33

(±)-Ethyl 9-hydroxy-12bβ-methyl-1,2,3,4,6,7,12,12b-octahydroindolo[2,3-a]quinolizine-1β-carboxylate 0.037 g. (0.000113 mole) of 1-[2-(5-hydroxy-indol-3-yl)-ethyl]-2-methyl-1,4,5,6-tetrahydronicotinate prepared according to Example 32 are dissolved in 1.6 ml. of a 1:1 aqueous hydrochloric acid solution, and the solution is allowed to stand at room temperature for 15 minutes. It is then diluted to three-fold of its volume with water, there are added 0.1 g. of tartaric acid and 0.5 g. of sodium carbonate (pH 10) and the mixture is extracted with chloroform. After drying over solid anhydrous magnesium sulfate the mixture is evaporated to dryness on a rotating evaporator, and the product is purified by column chromatography on 2 g. of silica gel (Geduran Si 60, 0.063–0.200 mm.) using toluene containing 20% of diethyl amine for the dilution.

Yield: 0.009 g. (24.3%) of a yellow oil $R_f$: 0.47 (Polygram SIL G/UV$_{254}$, toluene containing 20% of diethyl amine, u.v. light)

EXAMPLE 34

(±)-Ethyl 9-chloro-12bβ-methyl-1,2,3,4,6,7,12,12b-octahydroindolo[2,3-a]quinolizine-1β-carboxylate 6.24 g. (0.02 mole) of (±)-ethyl 12bβ-methyl-1,2,3,4,6,7,12,12b-octahydroindolo[2,3-a]quinolizine-1β-carboxylate (prepared according to Example 2) are refluxed in 15 ml. of sulfuryl chloride, in the presence of 0.025 g. of iodine for 30 minutes. Thereafter the excess of sulfuryl chloride is eliminated on a rotating evaporator, the residue is taken up in chloroform and washed with water. After drying over solid anhydrous magnesium sulfate the solvent is eliminated on a rotating evaporator, and the crude product is purified on 400 g. of silica gel (Geduran Si 60, 0.063–0.200 mm.) using cyclohexane containing 10% of diethyl amine as an eluent.

Yield: 2.2 g. (31.7%) of a slowly crystallizing oil

Melting point: 123° C. to 124° C.

$R_f$: 0.46 (Polygram SIL G/UV$_{254}$, cyclohexane containing 10% of diethyl amine, u.v. light)

EXAMPLE 35

Ethyl 1-[2-(1-benzyl-indol-3-yl)-ethyl]-2-methyl-1,4,5,6-tetrahydronicotinate

To a solution of 4.14 g. (0.02 mole) of (±)-ethyl 2-(3-chloropropyl)-acetoacetate in 20 ml. of chlorobenzene 5.0 g. (0.02 mole) of N-benzyl-tryptamine and 3.32 ml. (0.024 mole) of triethyl amine dried over potassium hydroxide are added, and the mixture is kept at 150° C. for three hours, allowing the chlorobenzene to distill off slowly.

After cooling the triethyl amine hydrochloride precipitate is filtered off, the filtrate is evaporated to dryness on a rotating evaporator, and the crude product is purified by chromatography on 200 g. of silicagel (Geduran Si 60, 0.063–0.200 mm.) using toluene containing 10% of diethyl amine as an eluent.

Yield: 6.0 g. (74.5%) of a yellow oil $R_f$: 0.71 (Polygram SIL G/UV$_{254}$, toluene containing 10% of diethyl amine, u.v. light)

EXAMPLE 36

(±)-Ethyl 12-benzyl-12bβ-methyl-1,2,3,4,6,7,12,12b-octahydroindolo[2,3-a]quinolizine-1β-carboxylate 0.201 g. (0.0005 mole) of ethyl 1-[2-(1-benzylindol-3-yl)-ethyl]-1,4,5,6-tetrahydronicotinate prepared according to Example 35 are dissolved in 2 ml. of dioxane, 1 ml. of concentrated hydrochloric acid is added to the solution, which is then allowed to stand at room temperature for two days. The reaction mixture is evaporated, dissolved in 5 ml. of dichloromethane, 3 ml. of water are added to the solution, which is then rendered alkaline with a 10% aqueous sodium carbonate solution. After separating the phases the aqueous part is washed with two 5-ml. portions of dichloromethane, the combined dichloromethane solution is dried over anhydrous magnesium sulfate, evaporated and purified by column chromatography on 15 g. of silica gel (Geduran Si 60, 0.063–0.200 mm.) using ethyl acetate containing 2% of triethyl amine as an eluent.

Yield: 0.022 g. (10.9%) of a brown oil $R_f$: 0.57 (Polygram SIL G/UV$_{254}$, ethyl acetate containing 2% of triethyl amine, u.v. light)

EXAMPLE 37

(±)-Ethyl 1β-benzyl-12,12bβ-dimethyl-1,2,3,4,6,7,12,12b-octahydroindolo[2,3-a]quinolizine-1α-carboxylate A solution of 1.75 ml. (0.0124 mole) of dry diisopropyl amine in 10 ml. of dry tetrahydrofurane is cooled to −50° C. under argon atmosphere, 6.85 ml. (0.011 mole) of a 1.6 molar solution of n-butyl-lithium in n-hexane are added to the solution, which is then stirred at −50° C. for 5 minutes and subsequently at −30° C. for 10 minutes. It is then cooled to −78° C., supplemented with 1.85 ml. (0.011 mole) of dry hexamethylphosphoric acid triamide and is stirred at this temperature for one hour. At −70° C. a solution of 0.979 g. (0.003 mole) of (±)-ethyl 12,12bβ-dimethyl-1,2,3,4,6,7,12,12b-octahydroindolo[2,3-a]quinolizine-1β-carboxylate prepared according to Example 15 in 20 ml. of dry tetrahydrofuran is added dropwise, whereupon the reaction mixture is stirred for 5 minutes at this temperature and for 30 minutes at 0° C. After the addition of 1.55 ml. (0.013 mole) of benzyl bromide, the mixture is stirred for further 30 minutes at 0° C. The external cooling is terminated, 50 ml. of a 25% aqueous sodium chloride solution are added to the reaction mixture, which is shaken, the phases are separated and the aqueous phase is extracted with 30 ml. of ether. The combined organic phase is dried over solid anhydrous magnesium sulfate and evaporated. The solid residue is purified by column chromatography on 20 g. of silica gel (Geduran Si 60, 0.063–0.200 mm.) using petroleum ether containing 10% of diethyl amine as an eluent.

Yield: 0.272 g. (21.8%) of an oily product solidifying upon standing

Melting point: 127° C. to 131° C.

$R_f$: 0.36 (Polygram SIL G/UV$_{254}$, petroleum ether containing 10% of diethyl amine, u.v. light)

Analysis for $C_{27}H_{32}N_2O_2$ (416.55): calculated: C 77.85; H 7.74; N 6.73%; found C 77.96; H 7.69; N 6.75%.

EXAMPLE 38

Ethyl 2-methyl-1-[2-(5-methoxy-indol-3-yl)-ethyl]-1,4,5,6-tetrahydronicotinate 0.209 g. (0.0011 mole) of 5-methoxytryptamine, 0.248 g. (0.0012 mole) of (±)-ethyl 2-(3-chloropropyl)-acetoacetate and 0.258 g. (0.002 mole) of dry diisopropylethyl amine are slightly boiled in 5 ml. of chlorobenzene for 45 minutes, under stirring. The precipitate is filtered off, washed with three 1-ml. portions of chlorobenzene and the combined chlorobenzene solution is evaporated. The residue is purified by column chromatography on 40 g. of silica gel (Geduran Si 60, 0.063–0.200 mm.) using toluene containing 10% of diethyl amine as an eluent.

Yield: 0.128 g. (34%) of an oil solidifying upon standing $R_f$: 0.49 (Polygram SIL G/UV$_{254}$, toluene containing 10% of diethyl amine, u.v. light)

EXAMPLE 39

(±)-Ethyl 12bβ-methyl-9-methoxy-1,2,3,4,6,7,12,12b-octahydroindolo[2,3-a]quinolizine-1β-carboxylate 2.57 g. (0.0135 mole) of 5-methoxytryptamine, 2.89 g. (0.014 mole) of (±)-ethyl 2-(3-chloropropyl)-acetoacetate ethyl ester and 3.61 g. (0.028 mole) of dry diisopropylethyl amine are slightly boiled in 50 ml. of chlorobenzene, under stirring for 45 minutes. The water formed is allowed to distill off continuously together with chlorobenzene. The precipitate is filtered off after cooling, washed with three 10-ml. portions of chlorobenzene and the combined chlorobenzene solution is evaporated. The residue (the crude ethyl 2-methyl-1-[2-(5-methoxy-indol-3-yl)-ethyl]-1,4,5,6-tetrahydronicotinate) is dissolved in 25 ml. of ethanol and a mixture of 25 ml. of concentrated hydrochloric acid and 25 ml. of water is added to the solution. After standing for 3 hours at room temperature, 50 ml. of water are added to the mixture, followed by the addition of 50 ml. of dichlormethane. The solution is rendered alkaline with sodium carbonate (pH 10), the phases are separated and the aqueous phase is extracted with three 25-ml. portions of dichloromethane. The combined dichloromethane solution is dried over solid anhydrous magnesium sulfate and evaporated. The residue is subjected to column chromatography on 400 g. of silica gel (Geduran Si 60, 0.063–0.200 mm.) using toluene containing 10% of triethyl amine as an eluent, to yield the desired product.

Yield: 1.45 g. (31%) of an oily product crystallizing upon standing

Melting point: 82° C. to 85° C.

$R_f$: 0.55 (Polygram SIL G/UV$_{254}$, toluene containing 10% of triethyl amine, u.v. light)

EXAMPLE 40

(±)-Ethyl 12bβ-methyl-9-methoxy-1,2,3,4,6,7,12,12b-octahydroindolo[2,3-a]quinolizine-1β-carboxylate hydrochloride To a solution of 0.684 g. (0.002 mole) of the crude base prepared in Example 39 in 5 ml. of isopropyl alcohol 0.36 ml. (0.0021 mole) of a 5.9 molar solution of hydrochloric acid in dry dioxane is added dropwise, under stirring. The product becomes crystalline in a short time and can be recrystallized from isopropanol.

Yield: 0.606 g. (80%)

Melting point: 254° C. to 256° C. (decomposition)

Analysis for $C_{20}H_{27}ClN_2O_3$ (378.88): calculated: C 63.40; H 7.18; N 7.39; $C_{ionic}$ 9.36%; found: C 63.25; H 7.10; N 7.37; $C_{ionic}$ 9.19%.

EXAMPLE 41

(±)-Ethyl 12bα-methyl-9-methoxy-1,2,3,4,6,7,12,12b-octahydroindolo[2,3-a]quinolizine-1β-carboxylate The title compound is obtained by collecting the $R_f$: 0.46 fractions during the chromatography of (±)-ethyl 12bβ-methyl-9-methoxy-1,2,3,4,6,7,12,12b-octahydroindolo[2,3-a]quinolizine-1β-carboxylate prepared according to Example 39.

Yield: 0.285 g. (6.2%) of a thick oil $R_f$: 0.46 (Polygram SIL G/UV$_{254}$, toluene containing 10% of triethyl amine, u.v. light)

EXAMPLE 42

Ethyl 2-methyl-1-[2-(6-methoxy-indol-3-yl)-ethyl]-1,4,5,6-tetrahydronicotinate 0.190 g. (0.001 mole) of 6-methoxy-tryptamine, 0.228 g. (0.0011 mole) of (±)-2-(3-chloropropyl)-acetoacetic acid ethyl ester and 0.258 g. (0.002 mole) of dry diisopropylethyl amine are slightly boiled in 5 ml. of chlorobenzene for 90 minutes, under stirring. The chlorobenzene is allowed to distill off slowly. The mixture is cooled. The precipitate obtained is filtered off, washed with three 1-ml. portions of chlorobenzene, and the combined chlorobenzene solution is evaporated. The residue is purified by column chromatography on 40 g. of silica gel (Geduran Si 60, 0.063–0.200 mm.) using toluene containing 10% of diethyl amine as an eluting agent.

Yield: 0.238 g. (37%) of an oil solidifying upon standing $R_f$: 0.35 (Polygram SIL G/UV$_{254}$, toluene containing 10% of diethyl amine, u.v. light)

EXAMPLE 43

(±)-Ethyl 12bβ-methyl-10-methoxy-1,2,3,4,6,7,12,12b-octahydroindolo[2,3-a]quinolizine-1β-carboxylate 0.099 g. (0.00029 mole) of ethyl 2-methyl-1-[2-(6-methoxy-indol-3-yl)-ethyl]-1,4,5,6-tetrahydronicotinate prepared according to Example 42 are dissolved in a mixture of 1.5 ml. of concentrated hydrochloric acid and 1.5 ml. of water and the solution is allowed to stand at room temperature for two hours. It is diluted with 5 ml. of water, the pH is rendered alkaline (pH 10) with sodium carbonate, and the mixture is extracted with three 10-ml. portions of dichloromethane. The dichloromethane solution is dried over solid anhydrous magnesium sulfate and evaporated. The curde product obtained is purified by column chromatography on 20 g. of silica gel (Geduran Si 60, 0.063–0.200 mm.) using tetrachloromethane containing 5% of diethyl amine as an eluent.

Yield: 0.085 g. (86%) of an oily product solidifying upon standing $R_f$: 0.42 (Polygram SIL G/UV$_{254}$, tetrachloromethane containing 5% of diethyl amine, u.v. light)

EXAMPLE 44

Ethyl 2-methyl-1-[2-(5-methyl-indol-3-yl)-ethyl]-1,4,5,6-tetrahydronicotinate 0.191 g. (0.0011 mole) of 5-methyl-tryptamine, 0.248 g. (0.0012 mole) of (±)-2-(3-chloropropyl)-acetoacetic acid ethyl ester and 0.258 g. (0.002 mole) of dry diisopropylethyl amine in 5 ml. of chlorobenzene are slightly boiled under stirring for 60 minutes, while chlorobenzene is allowed to distill off slowly. The precipitate separated out is filtered after cooling, washed with three 1-ml. portions of chlorobenzene, and the combined chlorobenzene solution is evaporated. The residue is purified by column chromatography in 40 g. of silica gel (Geduran Si 60, 0.063–0.200 mm.) using toluene containing 10% of diethyl amine as an eluent.

Yield: 0.135 g. (38%) of an oily product which solidifies upon standing $R_f$: 0.52 (Polygram SIL G/UV$_{254}$, toluene containing 10% of diethyl amine, u.v. light)

EXAMPLE 45

(±)-Ethyl 9,12bβ-dimethyl-1,2,3,4,6,7,12,12b-octahydroindolo[2,3-a]quinolizine-1β-carboxylate 5.05 g. (0.029 mole) of 5-methyl-tryptamine, 6.20 g. (0.03 mole) of (±)-2-(3-chloropropyl)-acetoacetic acid ethyl ester and 7.74 g. (0.06 mole) of dry diisopropylethyl amine in 100 ml. of chlorobenzene are slightly boiled for 60 minutes, with stirring, while the water formed is allowed to distill off slowly together with chlorobenzene. The precipitate separated out is filtered off after cooling, washed with three 15-ml. portions of chlorobenzene, and the combined chlorobenzene solution is evaporated. The residue, i.e. the crude ethyl 2-methyl-1-[2-(5-methylindol-3-yl)-ethyl]-1,4,5,6-tetrahydronicotinate, is stirred with a mixture of 45 ml. of concentrated hydrochloric acid and 45 ml. of water at room temperature for 30 minutes, whereupon it is decanted. 100 ml. of water and 25 ml. of dichloromethane are then added to the thick oily phase, the pH is adjusted to 10 with sodium carbonate, the phases are separated and the aqueous phase is extracted with two 25-ml. portions of dichloromethane. The combined dichloromethane solution is dried over solid anhydrous magnesium sulfate and is then evaporated. The crude product is purified by column chromatography on 500 g. of silica gel (Geduran Si 60, 0.063–0.200 mm.) using toluene containing 5% of diethyl amine as an eluent.

Yield: 3.05 g. (32%) of an oil crystallizing upon standing, which can be recrystallized from n-hexane Melting point: 104° C. to 108° C.

$R_f$: 0.54 (Polygram SIL G/UV$_{254}$, toluene containing 5% of diethyl amine, u.v. light).

EXAMPLE 46

(±)-Ethyl 9,12bβ-dimethyl-1,2,3,4,6,7,12,12b-octahydroindolo[2,3-a]quinolizine-1β-carboxylate The aqueous solution obtained by decantation following the cyclization in the presence of hydrochloric acid in the process described in Example 45 for the preparation of (±)-ethyl 9,12bβ-dimethyl-1,2,3,4,6,7,12,12b-octahydroindolo[2,3-a]quinolizine-1β-carboxylate, is diluted with 100 ml. of water, the pH is adjusted to 10 with sodium carbonate and the mixture is extracted with three 25-ml. portions of dichloromethane. The combined dichloromethane solution is dried over solid anhydrous magnesium sulfate and is then evaporated. The residue is subjected to column chromatography on 100 g. of silica gel (Geduran Si 60, 0.063–0.200 mm.) using toluene containing 5% of diethyl amine and subsequently cyclohexane containing 5% of diethyl amine and subsequently cyclohexane containing 5% of diethyl amine as an eluent, to yield the title compound.

Yield: 0.428 g. (4.5%) of a thick oil $R_f$: 0.31 (Polygram SIL G/UV$_{254}$, cyclohexane containing 5% of diethyl amine, u.v. light)

EXAMPLE 47

(±)-Ethyl 9,12bβ-dimethyl-1,2,3,4,6,7,12,12b-octahydroindolo[2,3-a]quinolizine-1β-carboxylate hydrochloride To a solution of 0.978 g. (0.003 mole) of the crude base obtained in Example 45 in 5 ml. of isopropyl alcohol 0.535 ml. (0.00315 mole) of a 5.9 molar solution of hydrochloric acid in dry dioxane is added dropwise, under stirring. The product precipitates in a crystalline form upon standing overnight.

Yield: 0.804 g. (74%)

Melting point: 244° C. to 247° C. (decomp.)

Analysis for $C_{20}H_{27}ClN_2O_2$ (362.88): calculated: C 66.19; H 7.50; N 7.72; Cl$_{ionic}$9.77%; found: C 66.07; H 7.40; N 7.56; Cl$_{ionic}$9.88%.

EXAMPLE 48

(±)-Ethyl 1β-butyl-12,12bβ-dimethyl-1,2,3,4,6,7,12,12b-octahydroindolo[2,3-a]-quinolizine-1α-carboxylate A solution of 1.75 ml. (0.0124 mole) of dry diisopropyl amine in 10 ml. of dry tetrahydrofurane is cooled to −50° C. under argon atmosphere. 6.85 ml. (0.011 mole) of a 1.6 molar solution of n-butyl-lithium in n-hexane are added to the first solution, which is then stirred at −50° C. for five minutes and subsequently at −30° C. for 10 minutes. The mixture is then cooled to −78° C., there are added 1.85 ml. (0.011 mole) of dry hexamethylphosphoric acid triamide, whereupon the mixture is stirred at the same temperature for one hour. At −70° C. 0.979 g. (0.003 mole) of (±)-ethyl 12,12bβ-dimethyl-1,2,3,4,6,7,12,12b-octahydroindolo[2,3-a]-quinolizine-1β-carboxylate prepared according to Example 15 dissolved in 20 ml. of dry tetrahydrofurane are added to the mixture, which is then stirred at this temperature for 5 minutes and subsequently at 0° C. for 30 minutes. The reaction mixture is supplemented with 1.5 ml. (0.013 mole) of butyl iodide and is then stirred for further 30 minutes at 0° C. The external cooling is terminated, 50 ml. of a 25% aqueous sodium chloride solution are added to the reaction mixture, it is shaken thoroughly and the phases are separated. The aqueous phase is extracted with 30 ml. of ether. The organic phases are combined, dried over solid anhydrous magnesium sulfate and evaporated. The residue is purified by column chromatography on 160 g. of a silica gel column (Geduran Si 60, 0.063–0.200 mm.) using toluene containing 0.5% of diethyl amine as an eluent.

Yield: 0.45 g. (39.2%) of an oil getting crystalline upon standing

Melting point: 110° C. to 114° C. (n-hexane)

$R_f$: 0.77 (Polygram SIL G/UV$_{254}$, toluene containing 0.5% of diethyl amine, u.v. light)

Analysis for $C_{24}H_{34}N_2O_2$ (382.53): calculated: C 75.35; H 8.96; N 7.32%; found: C 75.39; H 8.93; N 7.40%.

EXAMPLE 49

5-(3-Phenyl-propionyl)-6-(2-phenylethyl)-3,4-dihydro-2H-pyrane 2.8 g. (0.01 mole) of 1,7-diphenyl-heptane-3,5-dione (Ch. R. Hauser, T.M. Harris: J. Am. Chem. Soc. 81, 1154 (1959)) are dissolved in 100 ml. of acetone dried over potassium carbonate, 3.85 g. (0.012 mole) of chlorobromopropane, 1.38 g. (0.01 mole) of anhydrous potassium carbonate and 0.1 g. of anhydrous sodium iodide are added to the solution, which is then boiled for 24 hours. After cooling the potassium carbonate is filtered off and washed with acetone. The filtrate is evaporated on a rotating evaporator and the residue is purified by chromatography on 400 g. of a silica gel column (Geduran Si 60, 0.063–0.200 mm.) using petroleum ether containing 10% of ethyl acetate for the elution.

Yield: 0.8 g. (25%) of a pale yellow oil $R_f$: 0.31 (Polygram SIL G/UV$_{254}$, petroleum ether containing 10% of ethyl acetate, u.v. light)

Analysis for $C_{22}H_{24}O_2$ (320.41): calculated: C 82.46; H 7.55%; found: C 82.57; H 7.56%.

EXAMPLE 50

4-(3-Bromopropyl)-1,7-diphenyl-heptane-3,5-dione 2.3 g. (0.0072 mole) of 5-(3-phenyl-propionyl)-6-(2-phenylethyl)-3,4-dihydro-2H-pyrane prepared according to Example 49 are dissolved in 50 ml. of acetic acid containing 33% of hydrogen bromide and the solution is boiled for 4 hours. After cooling the mixture is poured onto ice water, and the aqueous phase is extracted with three 25-ml. portions of chloroform. The combined chloroform extract is washed acid-free with a 5% aqueous sodium bicarbonate solution and to neutral with water, dried over anhydrous solid magnesium sulfate and evaporated. The residue is purified by chromatography on 250 g. of a silica gel column (Geduran Si 60, 0.063–0.200 mm.) using petroleum ether containing 10% of ethyl acetate for the elution.

Yield: 0.56 g. (19.4%) of a pale yellow oil $R_f$: 0.21 (Polygram SIL G/UV$_{254}$, petroleum ether containing 10% of ethyl acetate, u.v. light)

Analysis for $C_{22}H_{25}BrO_2$ (401.34): calculated: C 65.83; H 6.28; Br 19.91%; found: C 65.74; H 6.25; Br 19.98%.

EXAMPLE 51

2-(2-Phenylethyl)-3-(3-phenylpropionyl)-1-[2-(indol-3-yl)-ethyl]-1,4,5,6-tetrahydropyridine 0.2 g. (0.000498 mole) of 4-(3-bromo-propyl)-1,7-diphenyl-heptane-3,5-dione prepared according to Example 50 are dissolved in 10 ml. of chlorobenzene, 0.16 g. (0.001 mole) of tryptamine are added to the solution, which is then boiled for 12 hours. After cooling the solution is evaporated to dryness on a rotating evaporator, in vacuum, the evaporation residue is carefully triturated with 50 ml. of chloroform, filtered and the chloroformic phase is evaporated. The residue is purified by chromatography on 40 g. of a silica gel column (Geduran Si 60, 0.063–0.200 mm.) using toluene containing 10% of diethyl amine as an eluent.

Yield: 0.122 g. (56%) of an oily material crystallizing upon standing

Melting point: 110° C. to 115° C.

$R_f$: 0.41 (Polygram SIL G/UV$_{254}$, toluene containing 10% of diethyl amine, u.v. light)

Analysis for $C_{32}H_{34}N_2O$ (462.61): calculated: C 83.08; H 7.41; N 6.06%; found: C 82.94; H 7.50; N 6.11%.

EXAMPLE 52

(±)-1β-(3-Phenylpropionyl)-12bβ-(2-phenylethyl)-1,2,3,4,6,7,12,12b-octahydroindolo[2,3-a]quinolizine 0.055 g. (0.000119 mole) of 2-(2-phenyl-ethyl)-3-(3-phenylpropionyl)-1-[2-(indol-3-yl)-ethyl]-1,4,5,6-tetrahydropyridine prepared according to Example 51 are dissolved in a mixture of 1 ml. of ethanol and 1 ml. of concentrated hydrochloric acid and the solution is allowed to stand at room temperature overnight. 10 ml. of water are added to the solution, the obtained precipitate is filtered off, suspended in 20 ml. of chloroform and stirred for 30 minutes with 20 ml. of a 5% aqueous sodium bicarbonate solution. The chloroform phase is washed with two 10-ml. portions of water, dried over solid anhydrous magnesium sulfate and evaporated. The solid residue is purified by chromatography on 10 g. of a silica gel column (Geduran Si 60, 0.063–0.200 mm.) using toluene containing 5% of diethyl amine for the solution.

Yield: 0.015 g. (27.3%) of a pale yellow oil $R_f$: 0.73 (Polygram SIL G/UV$_{254}$, toluene containing 5% of diethyl amine, u.v. light)

EXAMPLE 53

(±)-1β-(3-Phenylpropionyl)-12bα-(2-phenylethyl)-1,2,3,4,6,7,12,12b-octahydroindolo[2,3-a]quinolizine The title compound is obtained by collecting the $R_f$: 0.59 fractions during the chromatography of (±)-1β-(3-phenylpropionyl)-12bβ-(2-phenylethyl)-1,2,3,4,6,7,12,12b-octahydroindolo[2,3-a]quinolizine prepared in Example 52, and by evaporation of the collected fractions.

Yield: 0.013 g. (23.6%) of a pale yellow oil $R_f$: 0.59 (Polygram SIL G/UV$_{254}$, toluene containing 5% of diethyl amine, u.v. light).

The compounds of the formula (I) in addition to having per se pharmaceutical activity are also intermediates useful in the preparation of other compounds having per se pharmaceutical activity. The compounds of the formula (I) may be reduced to form the compounds of the formula (VII) which possess per se vasodilating activity. The compounds of the formula (VII) have the following formula:

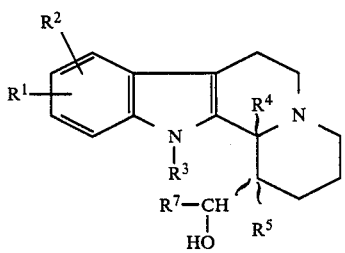

(VII)

wherein $R^1$, $R^2$, $R^3$, $R^4$ and $R^5$ are as defined above and $R^7$ is hydrogen, $C_1$ to $C_6$ alkyl, aryl or aralkyl having 1 to 6 carbon atoms in the alkyl moiety.

The compounds of the formula (VII) are prepared by reducing the compounds of the formula (I), and if desired, subjecting a 12b-substituted-1-hydroxymethyl-octahydroindolo-(2,3-a)quinolizine derivative of the formula (VII) obtained, in which $R^1$ and/or $R^2$ is halogen or a nitro group and/or $R^3$ stands for a benzyl group, $R^4$, $R^5$ and $R^7$ are as defined above, to a repeated reduction, and/or if desired, treating a 12b-substituted 1-hydroxymethyl-octahydroindolo(2,3-a)quinolizine of the formula (VII) obtained, with an acid, or treating an acid addition salt of a 12b-substituted 1-hydroxymethyl-octahydroindolo(2,3-a)quinolizine derivative of the formula (VII) obtained, with a base, and/or separating an isomeric mixture obtained into the respective isomers, and/or subjecting a racemic 12b-substituted-1-hydroxymethyl-octahydroindolo(2,3-a)quinolizine derivative of the formula (VII) obtained to resolution.

The compounds of the formula (VII) can be advantageously used in therapy in the treatment of diseases accompanied by vasoconstriciton especially diseases where peripheral blood flow is restricted. In the case of parenteral administration, the expected dose is 0.1 to 1.0 mg/kg of body weight, while in the case of oral administration, the dosage is 1 to 10 mg/kg of body weight, just the same as when the formula (I) compounds are administered.

More details on the compounds of the formula (I) may be found in commonly assigned Hungarian Patent Application 1518/85.

The following examples show how to convert the compounds of the formula (I) to the compounds of the formula (VII).

The compounds of the formula (VII) are prepared from the compounds of the formula (I) according to the following examples:

EXAMPLE 54

($\pm$)-1$\beta$-Hydroxymethyl-12b$\beta$-methyl-1,2,3,4,6,7,12,12b-octahydroindolo[2,3-a]quinolizine To a suspension of 5.7 g. (0.15 mole) of lithium aluminium hydride in 150 ml. of dry tetrahydrofuran a solution of 8.55 g. (0.0274 mole) of ($\pm$)-ethyl 12b$\beta$-methyl-1,2,3,4,6,7,12,12b-octahydroindolo[2,3-a]quinolizine-1$\beta$-carboxylate in 50 ml. of dry tetrahydrofuran is added dropwise, under argon atmosphere, at room temperature in 20 minutes, and the mixture is stirred at room temperature for one hour. Under ice cooling and stirring 5.7 ml. of water, 5.7 ml. of a 15% aqueous sodium hydroxide solution and subsequently 17.1 ml. of water are added carefully, dropwise. The precipitate is filtered off, washed with three 20-ml. portions of tetrahydrofuran, the combined tetrahydrofurane solution is dried over solid anhydrous magnesium sulfate and evaporated.

Yield: 6.28 g. (85%)

Melting point: 183° to 185° C.

$R_f$: 0.26 (Polygram SIL G/UV$_{254}$, ethyl acetate containing 10% of triethyl amine, u.v. light)

EXAMPLE 55

($\pm$)-1$\beta$-Hydroxymethyl-12b$\beta$-methyl-1,2,3,4,6,7,12,12b-octahydroindolo[2,3-a]quinolizine ethanesulfonate To a suspension of 4.59 g. (0.017 mole) of the base prepared according to the Example 54 in 17 ml. of isopropyl alcohol a solution of 1.925 g. (0.0175 mole) of ethanesulfonic acid in 17 ml. of isopropyl alcohol is added under stirring, and when the dissolution is complete the mixture is diluted with 50 ml. of acetone. The product is obtained in a crystalline form upon rubbing.

Yield: 5.99 g. (93%)

Melting point: 184° to 187° C. Analysis for $C_{19}H_{28}N_2O_4S$ (380.49): calculated: C 59.97%, H 7.42%, N 7.36%, S 8.43%; found: C 59.82%, H 7.21%, N 7.39%, S 8.39%.

EXAMPLE 56

(+)-1$\beta$-Hydroxymethyl-12b$\beta$-methyl-1,2,3,4,6,7,12,12b-octahydroindolo[2,3-a]quinolizine The title compound is prepared by the reduction of 8.02 g. (0.0257 mole) of (−)-12b$\beta$-methyl-1,2,3,4,6,7,12,12b-octahydroindolo[2,3-a]quinolizine-1$\beta$-carboxylic acid ethyl ester with lithium aluminium hydride, following the procedure and using the reactants in the quantities described in Example 54.

Yield: 6.74 g. (97%) of an oily product crystallizing upon standing

Melting point: 187° to 188° C. $[\alpha]^{25}_D = +17.4°$ (c=2.0; ethanol)

$R_f$: 0.26 (Polygram SIL G/UV$_{254}$, ethyl acetate containing 10% of triethyl amine, u.v. light)

EXAMPLE 57

(+)-1$\beta$-Hydroxymethyl-12b$\beta$-methyl-1,2,3,4,6,7,12,12b-octahydroindolo[2,3-a]quinolizine ethanesulfonate To a suspension of 6.48 g. (0.024 mole) of the base according to Example 56 in 10 ml. of ethanealcohol a solution of 2.64 g. (0.024 mole) of ethanesulfonic acid in 5 ml. of isopropyl alcohol is added, the mixture is boiled to complete dissolution and is subsequently diluted portionwise with 200 ml. of acetone. The title compound is obtained as a crystalline product.

Yield: 7.79 g. (85%)

Melting point: 238° to 242° C. $[\alpha]^{25}_D = +15.4°$ (c=2.0; ethanol)

Analysis for $C_{19}H_{28}N_2O_4S$ (380.49): calculated: C 59.97%, H 7.42%, N 7.36%, S 8.43%; found: C 60.04%, H 7.43%, N 7.35%, S 8.25%.

EXAMPLE 58

(−)-1α-Hydroxymethyl-12bβ-methyl-1,2,3,4,6,7,12,12b-octahydroindolo[2,3-a]quinolizine The title compound is prepared by the reduction of 7.10 g. (0.0227 mole) of (+)-ethyl 12bα-methyl-1,2,3,4,6,7,12,12b-octahydroindolo[2,3-a]quinolizine-1α-carboxylate with lithium aluminium hydride, following the procedure and using the reactants in the quantities described in Example 54.

Yield: 6.08 g. (99%) of an oily product crystallizing upon standing

Melting point: 185° to 187° C. $[\alpha]^{22}_D = -17.2°$ (C=2.0; ethanol) $R_f$=0.26 (Polygram SIL G/UV$_{254}$, ethyl acetate containing 10% of triethyl amine, u.v. light)

EXAMPLE 59

(−)-1α-Hydroxymethyl-12bα-methyl-1,2,3,4,6,7,12,12b-octahydroindolo[2,3-a]quinolizine ethanesulfonate To a suspension of 6.00 g. (0.0222 mole) of the base prepared according to Example 58 in 10 ml. of acetone a solution of 2.44 g. (0.0222 mole) of ethanesulfonic acid in 5 ml. of isopropyl alcohol is added and the mixture is diluted with 5 ml. of acetone. The precipitated solid is dissolved by heating, and the solution is portionwise diluted with 185 ml. of acetone to yield the title compound in a crystalline form.

Yield: 6.27 g. (74%)

Melting point: 185° to 188° C. (the product solidifies and remelts at 238° to 239° C.) $[\alpha]^{22}_D = -15.0°$ (c=2.0; ethanol)

Analysis for $C_{19}H_{28}N_2O_4S$ (380.49): calculated: C 59.97%, H 7.42%, N 7.36%, S 8.43%; found: C 59.97%, H 7.74%, N 7.34%, S 8.33%.

EXAMPLE 60

(±)-1β-Hydroxymethyl-12bα-methyl-1,2,3,4,6,7,12,12b-octahydroindolo[2,3-a]quinolizine A solution of 0.624 g. (0.002 mole) of (±)-ethyl 12bα-methyl-1,2,3,4,6,7,12,12b-octahydroindolo[2,3-a]quinolizine-1β-carboxylate in 3 ml. of dry tetrahydrofurane is added dropwise to a suspension of 0.600 g. (0.016 mole) of lithium aluminium hydride in 20 ml. of dry tetrahydrofuran under argon atmosphere, at room temperature with stirring, in 10 minutes. The mixture is stirred for further one hour, whereupon 0.6 ml. of water, 0.6 ml. of a 15% aqueous sodium hydroxide solution and subsequently 1.8 ml. of water are added carefully, dropwise, under ice cooling and vigorous stirring. The precipitate is filtered off, washed with three 2-ml. portions of tetrahydrofuran, the combined tetrahydrofuran solution is dried over solid anhydrous magnesium sulfate and evaporated. The residue (0.445 g.) is purified by column chromatography on silica gel (40 g., Geduran Si 60, 0.063 to 0.200 mm.) using ethyl acetate containing 10% of triethyl amine for the elution and subsequent recrystallization from 5 ml. of 1,2-dichloroethane.

Yield: 0.180 g. (33%)

Melting point: 209° to 211° C.

$R_f$=0.45 (Polygram SIL G/UV$_{254}$, ethyl acetate containing 10% of triethyl amine, u.v. light)

EXAMPLE 61

(±)-1β-Hydroxymethyl-12bα-methyl-1,2,3,4,6,7,12,12b-octahydroindolo[2,3-a]quinolizine ethanesulfonate To a suspension of 1.50 g. (0.00555 mole) of the base prepared according to Example 60 in 25 ml. of isopropyl alcohol a solution of 0.611 g. (0.00555 mole) of ethanesulfonic acid in 5 ml. of isopropyl alcohol is added, the base is dissolved by heating and the solution is evaporated on a rotating evaporator. The foamy residue is dissolved in 3 ml. of isopropyl alcohol and the solution is diluted with 150 ml. of acetone. The product becomes crystalline slowly, upon rubbing.

Yield: 1.60 g. (76%)

Melting point: 189° to 193° C.

Analysis for $C_{19}H_{28}N_2O_4S$ (380.49): calculated: C 59.97%, H 7.42%, N 7.36%, S 8.43%; found: C 59.84%, H 7.70%, N 7.31%, S 8.25%.

EXAMPLE 62

(±)-1β-Hydroxymethyl-12,12bβ-dimethyl-1,2,3,4,6,7,12,12b-octahydroindolo[2,3-a]quinolizine A solution of 0.420 g. (0.00128 mole) of (±)-ethyl 12,12bβ-dimethyl-1,2,3,4,6,7,12,12b-octahydroindolo[2,3-a]quinolizine-1β-carboxylate in 30 ml. of dry tetrahydrofuran is added dropwise to a suspension of 0.380 g. (0.01 mole) of lithium aluminium hydride in 20 ml. of dry tetrahydrofuran under argon atmosphere, at room temperature in ten minutes, and the mixture is stirred for another hour at room temperature. Under ice cooling and stirring 0.5 ml. of water and 0.5 ml. of a 15% aqueous sodium hydroxide solution are carefully added followed by a dropwise addition of 1.5 ml. of water. The precipitate is filtered off, washed with tetrahydrofuran and the solution is evaporated. The solid residue is purified by column chromatography on silica gel (40 g. of Geduran Si 60, 0.063 to 0.200 mm.) using ethyl acetate containing 10% of diethyl amine as an eluent.

Yield: 0.285 g. (78%) of the title compound, which can be further purified by crystallization from ethyl acetate.

Melting point: 170° to 174° C.

$R_f$: 0.35 (Polygram SIL G/UV$_{254}$, ethyl acetate containing 10% of diethyl amine, u.v. light)

EXAMPLE 63

(±)-1β-Ethyl-1α-hydroxymethyl-12bβ-methyl-1,2,3,4,6,7,12,12b-octahydroindolo[2,3-a]quinolizine A solution of 0.075 g. (0.00022 mole) of (±)-ethyl 1β-ethyl-12bβ-methyl-1,2,3,4,6,7,12,12b-octahydroindolo-[2,3-a]quinolizine-1α-carboxylate in 0.6 ml. of dry tetrahydrofuran is added dropwise to a suspension of 0.084 g. (0.0022 mole) of lithium aluminium hydride in 2 ml. of dry tetrahydrofuran at room temperature, with stirring, under argon atmosphere, and the mixture is stirred for further one hour. The excess of the reducing agent is decomposed by the addition of 0.1 ml. of water, 0.1 ml. of a 15% aqueous sodium hydroxide solution and 0.3 ml. of water dropwise, the aluminium hydroxide precipitate is filtered off and washed with three 1-ml. portions of tetrahydrofuran. The combined tetrahydrofuran solution is dried over solid anhydrous magnesium sulfate and evaporated to yield the pure title compound.

Yield: 0.064 g. (97%) of a foamy material

R_f: 0.32 (Polygram SIL G/UV$_{254}$, tetrachloromethane containing 5% of diethyl amine, u.v. light)

EXAMPLE 64

(±)-1α-Hydroxymethyl-1β,12,12bβ-trimethyl-1,2,3,4,6,7,12,12b-octahydroindolo[2,3-a]quinolizine A solution of 0.340 g. (0.001 mole) of (±)-ethyl 1β,12,12bβ-trimethyl-1,2,3,4,6,7,12,12b-octahydroindolo[2,3-a]quinolizine-1α-carboxylate in 20 ml. of dry tetrahydrofuran is added dropwise to a suspension of 0.300 g. (0.00789 mole) of lithium aluminium hydride in 30 ml. of dry tetrahydrofuran under argon atmosphere, at room temperature, in 10 minutes, and the mixture is stirred at room temperature for further 4 hours. Under ice cooling and stirring 0.3 ml. of water and subsequently 0.3 ml. of a 15% aqueous sodium hydroxide solution are carefully added to the mixture, followed by a dropwise addition of 1.2 ml. of water. The precipitate is filtered off, washed with tetrahydrofuran, the combined tetrahydrofuran solution is dried over solid anhydrous magnesium sulfate and evaporated.

Yield: 0.197 g. (66%)
Melting point: 131° to 134° C.
R_f: 0.69 (Polygram SIL G/UV$_{254}$, ethyl acetate containing 1% of diethyl amine, u.v. light)

EXAMPLE 65

A- and B-epimers of (±)-1β(1-hydroxyethyl)-12bβ-methyl-1,2,3,4,6,7,12,12b-octahydroindolo[2,3-a]-quinolizine 0.266 g. (0.007 mole) of sodium borohydride are added to a solution of 0.198 g. (0.0007 mole) of 1β-acetyl-12bβ-methyl-1,2,3,4,6,7,12,12b-octahydroindolo[2,3-a]quinolizine in 10 ml. of dry methanol in small portions, within 10 minutes, and the mixture is allowed to stand at room temperature for two hours. After the addition of 5 ml. of acetone the solution is allowed to stand for an additional 10 minutes, whereupon it is evaporated and 5 ml. of acetone are distilled off. To the residue there are added 10 ml. of water and 10 ml. of dichloromethane, the mixture is thoroughly shaken and the phases are separated. The aqueous part is washed with two 10-ml. portions of dichloromethane, dried over anhydrous magnesium sulfate and evaporated. The epimeric mixture obtained is separated into its components by chromatography on 40 g. of silica gel (Geduran Si 60, 0.063-0.200 mm.) using toluene containing 10% of diethyl amine as an eluent.

A-epimer
Yield: 0.090 g. (45%) of a foamy material
R_f: 0.43 (Polygram SIL G/UV$_{254}$, toluene containing 10% of diethyl amine, u.v. light)

B-epimer
Yield: 0.107 g. (54%) of a foamy material
R_f: 0.28 (Polygram SIL G/UV$_{254}$, toluene containing 10% of diethyl amine, u.v. light)

EXAMPLE 66

A- and B-epimers of (±)-1β-(1-hydroxyethyl)-12bβ-methyl-1,2,3,4,6,7,12,12b-octahydroindolo-[2,3-a]quinolizine 0.099 g. (0.00035 mole) of 1β-acetyl-12bβ-methyl-1,2,3,4,6,7,12,12b-octahydroindolo[2,3-a]quinolizine are hydrogenated in 5 ml. of ethanol, in the presence of 1 g. of Raney nickel catalyst, at room temperature, under atmospheric pressure for 25 hours. The catalyst is filtered off, the solution is evaporated and the residue is separated into its components by chromatography on 40 g. of silica gel (Geduran Si 60, 0.063-0.200 mm.) using toluene containing 10% of diethyl amine as an eluent.

A-epimer
Yield: 0.015 g. (15%)
R_f: 0.43 (Polygram SIL G/UV$_{254}$, toluene containing 10% of diethyl amine, u.v. light)

B-epimer
Yield: 0.082 g. (82%)
R_f: 0.28 (Polygram SIL G/UV$_{254}$, toluene containing 10% of diethyl amine, u.v. light)

EXAMPLE 67

(±)-9-Bromo-1β-hydroxymethyl-12bβ-methyl-1,2,3,4,6,7,12,12b-octahydroindolo[2,3-a]-quinolizine 0.104 g. (0.0031 mole) of sodium borohydride are dissolved in 1 ml. of dry diethylene glycol dimethyl ether under argon atmosphere, with stirring and after stirring for several minutes 0.391 g. (0.001 mole) of (±)-ethyl 9-bromo-12bβ-methyl-1,2,3,4,6,7,12,12b-octahydroindolo[2,3-a]quinolizine-1β-carboxylate are added to the solution. Thereafter 0.140 g. (0.00105 mole) of anhydrous aluminium (III) chloride are added to the mixture under vigorous stirring, which is then stirred at room temperature for one hour and at 100° C. for an additional one hour. The mixture is allowed to cool to room temperature. It is then poured onto a mixture of 5 g. of broken ice and 0.7 ml. of concentrated hydrochloric acid, the mixture is rendered alkaline with a 10% aqueous sodium carbonate solution, extracted with chloroform, dried over solid anhydrous magnesium sulfate and evaporated. The crude product is purified by chromatography on 30 g. of silica gel (Geduran Si 60, 0.063-0.200 mm.) using toluene containing 10% of diethyl amine for the elution.

Yield: 0.180 g. (52%)
Melting point: 194° to 196° C.
R_f: 0.27 (Polygram SIL G/UV$_{254}$, ethyl acetate containing 5% of triethyl amine, u.v. light)

EXAMPLE 68

(±)-10-Bromo-1β-hydroxymethyl-12bβ-methyl-1,2,3,4,6,7,12,12b-octahydroindolo[2,3-a]quinolizine Following the procedure described in Example 67 but starting from 0.391 g. (0.001 mole) of (±)-ethyl10-bromo-12bβ-methyl-1,2,3,4,6,7,12,12b-octahydroindolo[2,3-a]quinolizine-1β-carboxylate, and purifying the crude product obtained on 30 g. of silica gel (Geduran Si 60, 0.063-0.200 mm.) using toluene containing 20% of diethyl amine as an eluent, the title compound is obtained.

Yield: 0.230 g. (66%)
Melting point: 218° to 220° C.
R_f: 0.18 (Polygram SIL G/UV$_{254}$, toluene containing 20% of diethyl amine, u.v. light)

EXAMPLE 69

(±)-8,9-Dibromo-1β-hydroxymethyl-12bβ-methyl-1,2,3,4,6,7,12,12b-octahydroindolo[2,3-a]quinolizine Following the procedure described in Example 67 but starting from 0.130 g. (0.000276 mole) of (±)-ethyl 8,9-dibromo-12bβ-methyl-1,2,3,4,6,7,12,12b-octahydroindolo[2,3-a]quinolizine-1β-carboxylate and purifying the crude product on 20 g. of silica gel (Geduran Si 60, 0.063–0.200 mm.) using toluene containing 20% of diethyl amine as an eluent, the title compound is obtained.

Yield: 0.054 g. (46%)

$R_f$: 0.27 (Polygram SIL G/UV$_{254}$, toluene containing 20% of diethyl amine, u.v. light)

EXAMPLE 70

(±)-1β-Hydroxymethyl-12bβ-methyl-8-nitro-1,2,3,4,6,7,12,12b-octahydroindolo[2,3-a]quinolizine Following the procedure described in Example 67 but starting from 0.357 g. (0.001 mole) of (±)-ethyl 12bβ-methyl-8-nitro-1,2,3,4,6,7,12,12b-octahydroindolo[2,3-a]quinolizine-1β-carboxylate and purifying the crude product obtained by chromatography on 30 g. of silica gel (Geduran Si 60, 0.063–0.200 mm.) using toluene containing 20% of diethyl amine as an eluent, the title compound is obtained.

Yield: 0.080 g. (25%)

Melting point: 246° to 248° C.

$R_f$: 0.2 (Polygram SIL G/UV$_{254}$, toluene containing 20% of diethyl amine, u.v. light)

EXAMPLE 71

(±)-1β-Hydroxymethyl-12bβ-methyl-10-nitro-1,2,3,4,6,7,12,12b-octahydroindolo[2,3-a]quinolizine Following the procedure described in Example 67 but starting from 0.357 g. (0.001 mole) of (±)-ethyl 12bβ-methyl-10-nitro-1,2,3,4,6,7,12,12b-octahydroindolo[2,3-a]quinolizine-1β-carboxylate and purifying the crude product obtained by chromatography on 30 g. of silica gel (Geduran Si 60, 0.063–0.200 mm.) using toluene containing 10% of diethyl amine as an eluent, the title compound is obtained.

Yield: 0.165 g. (52%)

Melting point: 196° to 198° C.

$R_f$: 0.17 (Polygram SIL G/UV$_{254}$, toluene containing 10% of diethyl amine, u.v. light)

EXAMPLE 72

(±)-10-Amino-1β-hydroxymethyl-12bβ-methyl-1,2,3,4,6,7,12,12b-octahydroindolo[2,3-a]quinolizine 1.40 g. (0.0105 mole) of anhydrous aluminium(III) chloride are dissolved in 50 ml. of dry ether under stirring and ice cooling, and the solution is added dropwise to a suspension of 0.4 g. (0.0105 mole) of lithium aluminium hydride in 50 ml. of dry ether, under stirring and ice cooling, in argon atmosphere. Thereafter, the suspension is boiled with stirring so that the refluxing ether should dissolve from an extractor 0.357 g. (0.001 mole) of (±)-ethyl 12bβ-methyl-10-nitro-1,2,3,4,6,7,12,12b-octahydroindolo[2,3-a]quinolizine-1β-carboxylate. When the dissolution is complete (about 10 minutes) the mixture is refluxed for further five hours, whereupon 25 ml. of water are added under cooling and stirring followed by the dissolution of 4.0 g. of sodium hydroxide. After stirring for 30 additional minutes the aqueous phase is washed with four 25-ml. portions of ether, the combined organic phase is dried over solid anhydrous magnesium sulfate and evaporated. The crude product is purified by chromatography on 30 g. of silica gel (Geduran Si 60, 0.063–0.200 mm.) using toluene containing 30% of diethyl amine as an eluent.

Yield: 0.13 g. (46%)

$R_f$: 0.17 (Polygram SIL G/UV$_{254}$, toluene containing 30% of diethyl amine, u.v. light)

EXAMPLE 73

(±)-10-Amino-1β-hydroxymethyl-12bβ-methyl-1,2,3,4,6,7,12,12b-octahydroindolo[2,3-a]quinolizine 0.10 g. (0.0003 mole) of (±)-1β-hydroxymethyl-12bβ-methyl-10-nitro-1,2,3,4,6,7,12,12b-octahydroindolo[2,3-a]quinolizine are dissolved in 10 ml. of dry ethanol (as to the preparation see Example 71) and the solution is hydrogenated in the presence of 0.2 g. of a 10% palladium-on-charcoal catalyst. When the hydrogen uptake ceases, the catalyst is filtered off, washed with two 2-ml. portions of ethanol and the product is isolated by evaporation on a rotating evaporator.

Yield: 0.09 g. (99%)

$R_f$: 0.17 (Polygram SIL G/UV$_{254}$, toluene containing 30% of diethyl amine, u.v. light)

EXAMPLE 74

(±)-1β-Hydroxymethyl-12-benzyl-12bβ-methyl-1,2,3,4,6,7,12,12b-octahydroindolo[2,3-a]quinolizine A solution of 0.04 g. (0.0001 mole) of (±)-ethyl 12-benzyl-12bβ-methyl-1,2,3,4,6,7,12,12b-octahydroindolo[2,3-a]quinolizine-1-carboxylate in 3 ml. of dry tetrahydrofuran is added dropwise to a suspension of 0.038 g. (0.001 mole) of lithium aluminium hydride in 2 ml. of dry tetrahydrofuran under argon atmosphere, at room temperature, and the mixture is stirred at room temperature for one hour. 0.05 ml. of water, 0.05 ml. of a 15% aqueous sodium hydroxide solution and subsequently 0.15 ml. of water are added to the reaction mixture carefully, dropwise, under ice cooling and stirring. The precipitate is filtered off, washed with tetrahydrofuran and the solution is evaporated. The solid residue is purified by chromatography on 10 g. of silica gel (Geduran Si 60, 0.063–0.200 mm.) using toluene containing 30% of diethyl amine as an eluent.

Yield: 0.012 g. (33.3%) of an yellow oil $R_f$: 0.60 (Polygram SIL G/UV$_{254}$, toluene containing 30% of diethyl amine, u.v. light)

EXAMPLE 75

(±)-1β-Hydroxymethyl-9-chloro-12bβ-methyl-1,2,3,4,6,7,12,12b-octahydroindolo[2,3-a]quinolizine 0.378 g. (0.0112 mole) of sodium borohydride are dissolved in 18 ml. of dry diethyleneglycol dimethyl ether under argon atmosphere, with stirring. After stirring for several minutes 2.08 g. (0.006 mole) of (±)-ethyl 9-chloro-12bβ-methyl-1,2,3,4,6,7,12,12b-octahydroindolo[2,3-a]quinolizine-1β-carboxylate are added to the solution. Thereafter, 0.504 g. (0.00378 mole) of anhydrous aluminium(III) chloride are added to the mixture under vigorous stirring, and the mixture is stirred at room temperature for one hour and at 100° C. for another hour. The mixture is allowed to cool to room temperature and is then poured onto a mixture of 15 g. of broken ice and 2.25 ml. of concentrated hydrochloric acid. The mixture is rendered alkaline with a 10% aqueous sodium carbonate solution, extracted with chloroform, dried over solid anhydrous magnesium sulfate and is then evaporated. The crude product obtained is purified by chromatography on 150 g. of silica gel (Geduran Si 60, 0.063–0.200 mm.) using toluene containing 20% of diethyl amine as an eluent.

Yield: 1.5 g. (82%) of the title compound, which can be further purified by crystallization from acetone.
Melting point: 200°–202° C.
$R_f$: 0.38 (Polygram SIL G/UV$_{254}$, toluene containing 20% of diethyl amine, u.v. light).

EXAMPLE 76

(±)-1β-Hydroxymethyl-9-chloro-12bβ-methyl-1,2,3,4,6,7,12,12b-octahydroindolo[2,3-a]quinolizine ethanesulfonate 1.2 g. (0.0039 mole) of the base prepared according to Example 75 are dissolved in 50 ml. of chloroform, whereupon 0.429 g. (0.0039 mole) of ethanesulfonic acid are added to the solution, under stirring and ice cooling. The crude product obtained by evaporation of the solvent is recrystallized from isopropyl alcohol.
Yield: 1.06 g. (65%)
Melting point: 160° to 163° C.
Analysis for $C_{19}H_{27}ClN_2O_4S$ (414.95): calculated: C 54.99%, H 6.56%, N 6.75%, Cl$_{tot}$.8.54%, S 7.73%; found: C 55.10%, H 6.71%, N 6.75%, Cl$_{tot}$.8.64%, S 7.69%.

EXAMPLE 77

(±)-9-Hydroxy-1β-hydroxymethyl-12bβ-methyl-1,2,3,4,6,7,12,12b-octahydroindolo[2,3-a]quinolizine A solution of 0.31 g. (0.00094 mole) of (±)-ethyl 9-hydroxy-12bβ-methyl-1,2,3,4,6,7,12,12b-octahydroindolo[2,3-a]quinolizine-1β-carboxylate in 20 ml. of dry tetrahydrofuran is added dropwise to a suspension of 0.38 g. (0.01 mole) of lithium aluminium hydride in 20 ml. of dry tetrahydrofuran, under argon atmosphere, at room temperature, in 5 minutes, whereupon the reaction mixture is stirred at room temperature for 30 minutes. 0.4 ml. of water, 0.4 ml. of a 15% aqueous sodium hydroxide solution and subsequently 1.2 ml. of water are added dropwise to the reaction mixture, under ice cooling and stirring. The precipitate is filtered off, washed with tetrahydrofuran and the solution is evaporated. The solid residue is purified by chromatography on 40 g. of silica gel (Geduran Si 60, 0.063–0.200 mm.) using toluene containing 20% of diethyl amine as an eluent.
Yield: 0.038 g. (14.1%) of a pale yellow oil
$R_f$: 0.31 (Polygram SIL G/UV$_{254}$, toluene containing 20% of diethyl amine, u.v. light)

EXAMPLE 78

(±)-12β-Phenyl-1β-hydroxymethyl-1,2,3,4,6,7,12,12b-octahydroindolo[2,3-a]quinolizine A solution of 0.442 g. (0.00118 mole) of (±)-ethyl 12α-phenyl-1,2,3,4,6,7,12,12b-octahydroindolo[2,3-a]quinolizine-1β-carboxylate in 4 ml. of dry tetrahydrofuran is added dropwise to a suspension of 0.46 g. (0.012 mole) of lithium aluminium hydride in 10 ml. of dry tetrahydrofuran, under argon atmosphere and stirring, at room temperature in 5 minutes. After stirring for an additional hour 0.5 ml. of water, 0.5 ml. of a 15% aqueous sodium hydroxide solution and subsequently 1.5 ml. of water are carefully added to the mixture, under ice cooling. The precipitate is filtered off, washed with three 5-ml. portions of tetrahydrofuran, the combined tetrahydrofuran extract is dried over solid anhydrous magnesium sulfate and evaporated. The crude product is purified by column chromatography on 50 g. of silica gel (Geduran Si 60, 0.063–0.200 mm.) using toluene containing 5% of diethyl amine for the elution.
Yield: 0.120 g. (31%) of the title compound crystallizing upon standing
Melting point: 243° to 247° C.
$R_f$: 0.45 (Polygram SIL G/UV$_{254}$, toluene containing 5% of diethyl amine, u.v. light).

EXAMPLE 79

A- and B-epimers of (±)-1β-(phenyl-hydroxymethyl)-12bβ-methyl-1,2,3,4,6,7,12,12b-octahydroindolo[2,3-a]quinolizine Into a solution of 0.955 g. (0.0028 mole) of (±)-1β-benzoyl-12bβ-methyl-1,2,3,4,6,7,12,12b-octahydroindolo[2,3-a]quinolizine in 50 ml. of dry methanol 1.60 g. (0.042 mole) of sodium borohydride are added at room temperature, with stirring, in small portions in 3 hours. After stirring for one additional hour, 25 ml. of acetone are added to the mixture, which is then stirred for 30 minutes, evaporated and 25 ml. of acetone are distilled off. The residue is diluted with 50 ml. of water and 50 ml. of dichloromethane and is thoroughly shaken. The phases are separated. The aqueous phase is washed with two 10-ml. portions of dichloromethane, and the combined dichloromethane solution is dried over solid anhydrous magnesium sulfate and evaporated. The epimeric mixture obtained is separated into its components by chromatography on 200 g. of silica gel (Geduran Si 60, 0.063–0.200 mm.) using toluene containing 10% of diethyl amine as an eluent.

A-epimer

Yield: 0.658 g. (68%) The product can be crystallized from chloroform.
Melting point: 212° to 214° C.
$R_f$: 0.62 (Polygram SIL G/UV$_{254}$, toluene containing 10% of diethyl amine, u.v. light)

B-epimer

Yield: 0.197 g (20%) of a thick oil solidifying upon standing
$R_f$: 0.31 (Polygram SIL G/UV$_{254}$, toluene containing 10% of diethyl amine, u.v. light).

EXAMPLE 80

Ethanesulfonate of the A-epimer of (±)-1β-(phenyl-hydroxymethyl)-12bβ-methyl-1,2,3,4,6,7,12,12b-octahydroindolo[2,3-a]quinolizine 0.623 g. (0.0018 mole) of the A-epimer base prepared according to Example 79 are dissolved in a warm mixture of 15 ml. of acetone and 5 ml. of isopropyl alcohol, whereupon a solution of 0.209 g. (0.0019 mole) of ethanesulfonic acid in 2.5 ml. of isopropyl alcohol is added dropwise, with stirring, in 5 minutes. After standing for a short time the product separates out in a crystalline form.
Yield: 0.685 g. (83%)
Melting point: 275° to 276° C. (decomp.)
Analysis for $C_{25}H_{32}N_2O_4S$ (456.58): calculated: C 65.76%, H 7.06%, N 6.14%, S 7.02%; found: C 65.87%, H 7.12%, N 6.14%, S 6.98%.

EXAMPLE 81

(±)-1β-Hydroxymethyl-12bβ-methyl-9-methoxy-1,2,3,4,6,7,12,12b-octahydroindolo[2,3-a]quinolizine A solution of 0.747 g. (0.00218 mole) of (±)-ethyl 12bβ-methyl-9-methoxy-1,2,3,4,6,7,12,12b-octahydroindolo[2,3-a]quinolizine-1β-carboxylate in 7 ml. of dry tetrahydrofuran is added dropwise, under argon atmosphere, in 10 minutes to a stirred suspension of 0.663 g. (0.0175 mole) of lithium aluminium hydride in 15 ml. of dry tetrahydrofuran, at room temperature. The reaction mixture is stirred for additional 80 minutes, whereupon 0.8 ml. of water and 0.8 ml. of a 15% aqueous sodium hydroxide solution are carefully added under ice cooling, followed by the dropwise addition of 2.4 ml. of water. The precipitate is filtered off, washed with three 2-ml. portions of tetrahydrofuran, the combined tetrahydrofuran solution is evaporated and 10 ml. of dry ethanol are distilled off. The crude product is purified by column chromatography on 80 g. of silica gel (Geduran Si 60, 0.063–0.200 mm.) using cyclohexane containing 10% of diethyl amine and 20% of isopropyl alcohol as an eluent.

Yield: 0.492 g. (75%) of the title compound, which can be crystallized from isopropyl alcohol.

Melting point: 189° to 191° C.

$R_f$: 0.43 (Polygram SIL G/UV$_{254}$, cyclohexane containing 10% of diethyl amine and 20% of isopropyl alcohol, u.v. light).

EXAMPLE 82

(±)-1β-Hydroxymethyl-12bβ-methyl-9-methoxy-1,2,3,4,6,7,12,12b-octahydroindolo[2,3-a]quinolizine ethanesulfonate To a suspension of 0.454 g. (0.0015 mole) of the base prepared according to Example 81 in 3 ml. of isopropyl alcohol a solution of 0.176 g. (0.0016 mole) of ethanesulfonic acid in 1 ml. of isopropyl alcohol is added. The base is dissolved under stirring, the mixture is evaporated and the residue is dissolved in 3 ml. of 1,2-dichloroethane. The product is obtained in a crystalline form after standing overnight.

Yield: 0.466 g. (76%)

Melting point: 177° to 181° C.

Analysis for $C_{20}H_{30}N_2O_5S$: calculated: C 58.51%, H 7.37%, N 6.82%, S 7.81%; found: C 58.47%, H 7.29%, N 6.78%, S 7.80%.

EXAMPLE 83

(±)-1β-hydroxymethyl-12bα-methyl-9-methoxy-1,2,3,4,6,7,12,12b-octahydroindolo[2,3-a]quinolizine A solution of 0.183 g. (0.000525 mole) of (±)-ethyl 12bα-methyl-9-methoxy-1,2,3,4,6,7,12,12b-octahydroindolo[2,3-a]quinolizine-1β-carboxylate in 2 ml. of dry tetrahydrofuran is added dropwise, in 10 minutes, under argon atmosphere to a suspension of 0.163 g. (0.00428 mole) of lithium aluminium hydride in 4 ml. dry tetrahydrofuran, while stirring the mixture. After stirring for additional 80 minutes 0.2 ml. of water and 0.2 ml. of a 15% aqueous sodium hydroxide solution are added dropwise to the reaction mixture under ice cooling, followed by the dropwise addition of 0.6 ml. of water. The precipitate is filtered off, washed with three 1-ml. portions of tetrahydrofuran, the combined tetrahydrofuran solution is evaporated and 5 ml. of dry ethanol are distilled off. The crude product is purified by column chromatography on 20 g. of silica gel (Geduran Si 60, 0.063–0.200 mm.) using cyclohexane containing 10% of diethyl amine and 20% of isopropyl alcohol as an eluent.

Yield: 0.117 g. (73%) of a foamy material $R_f$: 0.57 (Polygram SIL G/UV$_{254}$, cyclohexane containing 10% of diethyl amine and 20% of isopropyl alcohol, u.v. light).

EXAMPLE 84

(±)-9,12bβ-Dimethyl-1β-hydroxymethyl-1,2,3,4,6,7,12,12b-octahydroindolo[2,3-a]quinolizine A solution of 1.956 g. (0.006 mole) of (±)-ethyl 9,12bβ-dimethyl-1,2,3,4,6,7,12,12b-octahydroindolo[2,3-a]quinolizine-1β-carboxylate in 15 ml. of dry tetrahydrofuran are added dropwise, in 20 minutes, under argon atmosphere and stirring to a suspension of 1.824 g. (0.048 mole) of lithium aluminium hydride in 50 ml. of dry tetrahydrofuran, at room temperature. After stirring for two additional hours 1.8 ml. of water and 1.8 ml. of a 15% aqueous sodium hydroxide solution are added dropwise to the cooled solution, followed by dropwise addition of 5.4 ml. of water. The precipitate is filtered off, washed with three 10-ml. portions of tetrahydrofuran, and the combined tetrahydrofuran solution is dried over solid anhydrous magnesium sulfate and evaporated. The crude product is purified by chromatography on 200 g. of silica gel (Geduran Si 60, 0.063–0.200 mm.) using cyclohexane containing 10% of diethyl amine and 20% of ethanol as an eluent.

Yield: 1.175 g. (69%) of the title compound, crystallizing upon standing

Melting point: 173° to 176° C.

$R_f$: 0.55 (Polygram SIL G/UV$_{254}$, cyclohexane containing 10% of diethyl amine and 20% of ethanol, u.v. light).

EXAMPLE 85

(±)-9,12bβ-Dimethyl-1β-hydroxymethyl-1,2,3,4,6,7,12,12b-octahydroindolo[2,3-a]quinolizine ethanesulfonate A solution of 0.408 g. (0.0037 mole) of ethanesulfonic acid in 2 ml. of isopropyl alcohol are added dropwise, under stirring, in 5 minutes to a warm suspension of 0.989 g. (0.0035 mole) of the base prepared according to Example 84 in 7 ml. of isopropyl alcohol. The base is dissolved by stirring, the solution is evaporated and the residue is dissolved in 10 ml. of 1,2-dichloroethane. The mixture is allowed to stand overnight to yield the title compound in a crystalline form.

Yield: 1.220 g. (88%)

Melting point: 167° to 170° C.

Analysis for $C_{20}H_{30}N_2O_4S$ (394.52): calculated: C 60.88%, H 7.67%, N 7.10%, S 8.13%; found: C 60.97%, H 7.81%, N 7.12%, S 8.10%.

EXAMPLE 86

(±)-1β-Hydroxymethyl-12bβ-methyl-10-methoxy-1,2,3,4,6,7,12,12b-octahydroindolo[2,3-a]quinolizine The title compound is prepared from 0.075 g. (0.00022 mole) of (±)-ethyl 12bβ-methyl-10-methoxy-1,2,3,4,6,7,12,12b-octahydroindolo[2,3-a]quinolizine-1β-carboxylate following the procedure and using the reactants in the quantities described in Example 63. The crude product obtained is purified by chromatography on 20 g. of silica gel (Geduran Si 60, 0.063–0.200), using cyclohexane containing 10% of diethyl amine and 20% of ethanol for the elution.

Yield: 0.038 g. (58%) of a thick oil $R_f$: 0.49 (Polygram SIL G/UV$_{254}$, cyclohexane containing 10% of diethyl amine and 20% of ethanol, u.v. light).

EXAMPLE 87

(±)-1β-Butyl-12,12bβ-dimethyl-3α-hydroxymethyl-b 1,2,3,4,6,7,12,12b-octahydroindolo[2,3-a]quinolizine A solution of 0.100 g. (0.00026 mole) of (±)-ethyl 1β-butyl-12,12bβ-dimethyl-1,2,3,4,6,7,12,12b-octahydroindolo[2,3-a]quinolizine-1α-carboxylate in 5 ml. of dry tetrahydrofuran is added dropwise, under argon atmosphere and stirring to a suspension of 0.2000 g. (0.0053 mole) of lithium aluminium hydride in 5 ml. of dry tetrahydrofuran. During the addition the mixture is kept at boiling temperature. It is then refluxed for 8 hours. The excess of the reducing agent is decomposed by the successive, dropwise addition of 0.2 ml. of water, 0.2 ml. of a 15% aqueous sodium hydroxide solution and 0.6 ml. of water, under ice cooling. The precipitate is filtered off and washed with tetrahydrofuran. The combined tetrahydrofuran solution is dried over solid anhydrous magnesium sulfate and evaporated. The residue is purified by chromatography on 10 g. of silica gel (Geduran Si 60, 0.063–0.200 mm.) using n-hexane containing 25% of diethyl amine as an eluent.

Yield: 0.033 g. (36.6%) of an oily product solidifying upon standing

Melting point: 123° to 125° C.

$R_f$: 0.55 (Polygram SIL G/UV$_{254}$, n-hexane containing 25% of diethyl amine, u.v. light).

EXAMPLE 88

(±)-1β-Benzyl-12,12bβ-dimethyl-1α-hydroxymethyl-1,2,3,4,6,7,12,12b-octahydroindolo[2,3-a]quinolizine A solution of 0.100 g. (0.00024 mole) of (±)-ethyl 1β-benzyl-12,12bβ-dimethyl-1,2,3,4,6,7,12,12b-octahydroindolo[2,3-a]quinolizine-1α-carboxylate in 15 ml. of dry tetrahydrofuran is added dropwise, under argon atmosphere and stirring to a suspension of 0.200 g. (0.0053 mole) of lithium aluminium hydride in 15 ml. of dry tetrahydrofuran. During the addition the mixture is kept at boiling temperature. The mixture is then refluxed for 8 hours, while two further 0.200 g. portions of lithium aluminium hydride are added. Thereafter the excess of the reducing agent is decomposed by the successive, dropwise addition of 0.6 ml. of water, 0.6 ml. of a 15% aqueous sodium hydroxide solution and 2 ml. of water, under stirring and ice cooling. The precipitate is filtered off and washed with tetrahydrofuran. The combined tetrahydrofuran solution is dried over solid anhydrous magnesium sulfate and evaporated. The residue is purified by chromatography on 10 g. of silica gel (Geduran Si 60, 0.063–0.200 mm.) using a 1:1 mixture of petroleum ether containing 2% of diethyl amine and ethyl acetate as an eluent.

Yield: 0.023 g. (25.6%) of an oily product solidifying upon standing

Melting point: 185° to 190° C.

$R_f$: 0.45 (Polygram SIL G/UV$_{254}$, 1:1 mixture of petroleum ether containing 2% of diethyl amine and ethyl acetate, u.v. light).

EXAMPLE 89

(±)-1β-(1-Hydroxy-3-phenylpropyl)-12bα-(2-phenylethyl)-1,2,3,4,6,7,12,12b-octahydroindolo[2,3-a]quinolizine To a solution of 0.008 g. (0.000017 mole) of (±)-1β-(3-phenylpropionyl)-12bα-(2-phenylethyl)-1,2,3,4,6,7,12,12b-octahydroindolo[2,3-a]quinolizine in 1 ml. of dry methanol 0.032 g. (0.00084 mole) of sodium borohydride are added portionwise, under stirring. After standing for one hour 2 ml. of acetone are added to the mixture, which is then stirred for 30 minutes at room temperature, evaporated and a further 2-ml. portion of acetone is distilled off. The residue is supplemented with 3 ml. of water and extracted with three 3-ml. portions of dichloromethane. The dichloromethane solution is dried over solid anhydrous magnesium sulfate, evaporated and the residue is purified by column chromatography on 10 g. of silica gel (Geduran Si 60, 0.063–0.200 mm.) using cyclohexane containing 10% of diethyl amine as an eluent.

Yield: 0.005 g. (62%) of an oily product crystallizing upon standing.

Melting point: 158° to 163° C.

$R_f$: 0.21 (Polygram SIL G/UV$_{254}$, cyclohexane containing 10% of diethyl amine, u.v. light).

EXAMPLE 90

(±)-1β-(1-Hydroxy-3-phenylpropyl)-12bβ-(2-phenylethyl)-1,2,3,4,6,7,12,12b-octahydroindolo[2,3-a]quinolizine To a solution of 0.012 g. (0.000026 mole) of (±)-1β-(3-phenylpropionyl)-12bβ-(2-phenylethyl)-1,2,3,4,6,7,12,12b-octahydroindolo[2,3-a]quinolizine in 1.5 ml. of dry methanol 0.048 g. (0.00126 mole) of sodium borohydride are added portionwise, under stirring, in 1.5 hours. After standing overnight, 3 ml. of acetone are added to the solution, which is then stirred for 30 minutes at room temperature, evaporated and further 3 ml. of acetone are distilled off. The residue is diluted with 3 ml. of water and extracted with three 3-ml. portions of dichloromethane. The dichloromethane solution is dried over solid, anhydrous magnesium sulfate, evaporated and the residue is purified by chromatography on 10 g. of silica gel (Geduran Si 60, 0.063–0.200 mm.) using cyclohexane containing 10% of diethyl amine as an eluent.

Yield: 0.010 g. (83%) of an oily product solidifying upon standing $R_f$: 0.49 (Polygram SIL G/UV$_{254}$, cyclohexane containing 10% of diethyl amine, u.v. light).

We claim:

1. A compound of the Formula (I)

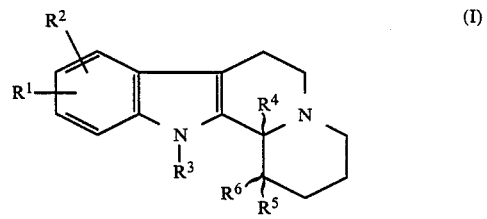

wherein $R^1$ and $R^2$ are the same or different and are hydrogen, halogen, nitro, $C_1$ to $C_6$ alkyl, $C_1$ to $C_6$ alkoxy or hydroxy;

$R^3$ and $R^5$ are the same or different and are hydrogen, $C_1$ to $C_6$ alkyl, phenyl, or phenyl-$C_1$ to $C_6$ alkyl;

$R^4$ is $C_1$ to $C_6$ alkyl, phenyl, or phenyl-$C_1$ to $C_6$ alkyl, and $R^6$ is alkoxycarbonyl having 1 to 6 carbon atoms in the alkoxy group, alkylcarbonyl having 1 to 6 carbon atoms in the alkyl group, phenylcarbonyl, or phenyl-$C_1$ to $C_6$-alkylcarbonyl;

or a cis or trans isomer, an optical isomer or a pharmaceutically acceptable acid addition salt thereof.

2. A vasodilating method of treatment which comprises the step of administering to a mammalian subject in need of said treatment, a vasodilatingly effective amount of a compound of the Formula (I) as defined in claim 1 or a pharmaceutically acceptable acid addition salt thereof.

3. A compound selected from the following group:
allyl 12b-methyl-1,2,3,4,6,7,12,12b-octahydroindolo[2,3-a]quinolizine-1-carboxylate;
ethyl 1-ethyl-12b-methyl-1,2,3,4,6,7,12,12b-octahydroindolo[2,3-a]quinolizine-1-carboxylate;
ethyl 12,12b-dimethyl-1,2,3,4,6,7,12,12b-octahydroindolo[2,3-a]quinolizine-1-carboxylate;
ethyl 9-bromo-12b-methyl-1,2,3,4,6,7,12,12b-octahydroindolo[2,3-a]quinolizine-1-carboxylate;
ethyl 10-bromo-12b-methyl-1,2,3,4,6,7,12,12b-octahydroindolo[2,3-a]quinolizine-1-carboxylate;
ethyl 8,9-dibromo-12b-methyl-1,2,3,4,6,7,12,12b-octahydroindolo[2,3-a]quinolizine-1-carboxylate;
ethyl 12b-methyl-10-nitro-1,2,3,4,6,7,12,12b-octahydroindolo[2,3-a]quinolizine-1-carboxylate;
ethyl 12b-methyl-8-nitro-1,2,3,4,6,7,12,12b-octahydroindolo[2,3-a]quinolizine-1-carboxylate;
ethyl 12b-methyl-8,10-dinitro-1,2,3,4,6,7,12,12b-octahydroindolo[2,3-a]quinolizine-1-carboxylate;
ethyl 1-ethyl-12,12b-dimethyl-1,2,3,4,6,7,12,12b-octahydroindolo[2,3-a]quinolizine-1-carboxylate;
ethyl 1,12,12b-trimethyl-1,2,3,4,6,7,12,12b-octahydroindolo[2,3-a]quinolizine-1-carboxylate;
1-acetyl-12b-methyl-1,2,3,4,6,7,12,12b-octahydroindolo[2,3-a]quinolizine;
1-benzoyl-12-methyl-1,2,3,4,6,7,12,12b-octahydroindolo[2,3-a]quinolizine;
ethyl 12b-phenyl-1,2,3,4,6,7,12,12b-octahydroindolo[2,3-a]quinolizine-1-carboxylate; or pharmaceutically acceptable salts thereof.

4. A pharmaceutical composition to effect vasodilation which comprises as active ingredient a vasodilatingly effective amount of the compound of the Formula (I), as defined in claim 1, a cis or trans isomer or a pharmaceutically acceptable acid addition salt thereof, in association with an inert pharmaceutical carrier or excipient.

* * * * *